(12) United States Patent
Kosmatopoulos et al.

(10) Patent No.: US 10,024,868 B2
(45) Date of Patent: Jul. 17, 2018

(54) **IDENTIFICATION, OPTIMIZATION AND USE OF SHARED HLA-B*0702 EPITOPES FOR IMMUNOTHERAPY**

(75) Inventors: Kostantinos (Kostas) Kosmatopoulos, Paris (FR); Jeanne Menez-Jamet, Montrouge (FR)

(73) Assignee: Vaxon Biotech, Paris (FR)

( * ) Notice: Subject to any disclaimer, the term of this patent is extended or adjusted under 35 U.S.C. 154(b) by 1115 days.

(21) Appl. No.: 13/377,091

(22) PCT Filed: Jun. 9, 2009

(86) PCT No.: PCT/IB2009/006332
§ 371 (c)(1),
(2), (4) Date: Feb. 22, 2012

(87) PCT Pub. No.: WO2010/143010
PCT Pub. Date: Dec. 16, 2010

(65) Prior Publication Data
US 2012/0142894 A1    Jun. 7, 2012

(51) Int. Cl.
*A61K 38/08* (2006.01)
*A61K 38/10* (2006.01)
*A61K 38/17* (2006.01)
*C07K 7/06* (2006.01)
*C07K 14/47* (2006.01)
*G01N 33/68* (2006.01)
*G05D 16/20* (2006.01)
*G11C 13/02* (2006.01)

(52) U.S. Cl.
CPC ......... *G01N 33/6878* (2013.01); *C07K 7/06* (2013.01); *C07K 14/4748* (2013.01); *G05D 16/20* (2013.01); *G11C 13/02* (2013.01); *C07K 2319/00* (2013.01)

(58) Field of Classification Search
None
See application file for complete search history.

(56) References Cited

U.S. PATENT DOCUMENTS 5,734,023 A * 3/1998 Nag .................. C07K 14/70539
424/185.1
7,698,688 B2 * 4/2010 Fujiwara ............... G06F 9/4448
704/8
9,340,577 B2 * 5/2016 Grey ........................ C07K 7/06
2006/0263381 A1   11/2006 Kosmatopoulos et al.
2007/0055049 A1 * 3/2007 Grey ...................... A61K 39/02
530/350
2007/0083334 A1 * 4/2007 Mintz .................... G06F 19/24
702/19
2011/0318380 A1 * 12/2011 Brix ................... A61K 39/0011
424/193.1

FOREIGN PATENT DOCUMENTS

| WO | WO199713858 A2 * | 4/1997 |
| WO | 2001/042267 | 6/2001 |
| WO | WO2003008537 A2 * | 1/2003 |
| WO | 2003/083124 | 10/2003 |
| WO | WO2003104428 A2 * | 12/2003 |
| WO | 2008/010010 | 1/2008 |
| WO | 2008/010098 | 1/2008 |

OTHER PUBLICATIONS

Mo et al (J. Immunol. 2000, 64: 4003-4010).*
Comber and Philip (Ther Adv. Vacc. 2014 2(3): 77-89).*
A_GENESEQ A0G47171 (May 28, 2008).*
Sewell, A.K. (Nature Reviews, Immunology, 2012, 12: 669-677).*
ADK50290 (Nov. 4).*
A_GENESEQ Accession No. AAW16332 (Sep. 1997).*
Tanzarella, Identification of Promiscuous T-Cell Epitope Encoded by Multiple Members of MAGE Family, Cancer Research, 59, 2668-2674, 1999.
Graff-Dubois, Generation of CTL Recognizing an HLA-A*0201-Restricted Epitope Shared by MAGE-A1, -A2, -A3, -A4,-A6, -A10, and -A12 Tumor Antigens: Implication in a Broad-Spectrum Tumor Immunotherapy, Journal of Immunology, 169, 575-580, 2002.
International Search Report for PCT/IB2009/006332, dated Sep. 14, 2010.

* cited by examiner

Primary Examiner — Gerald R Ewoldt
Assistant Examiner — Marianne Dibrino
(74) Attorney, Agent, or Firm — Morgan, Lewis & Bockius LLP

(57) ABSTRACT

The present invention provides novel methods and materials for efficiently treating patients having an HLA-B*0702 phenotype, based on peptides representing shared epitopes of tumor antigens. In particular, the invention relates to a method for identifying a HLA-B*0702-restricted peptide which can trigger a cytotoxic response against several antigens from one single multigenic family, and to several such epitopes.

9 Claims, 2 Drawing Sheets

Figure 1

Figure 2:
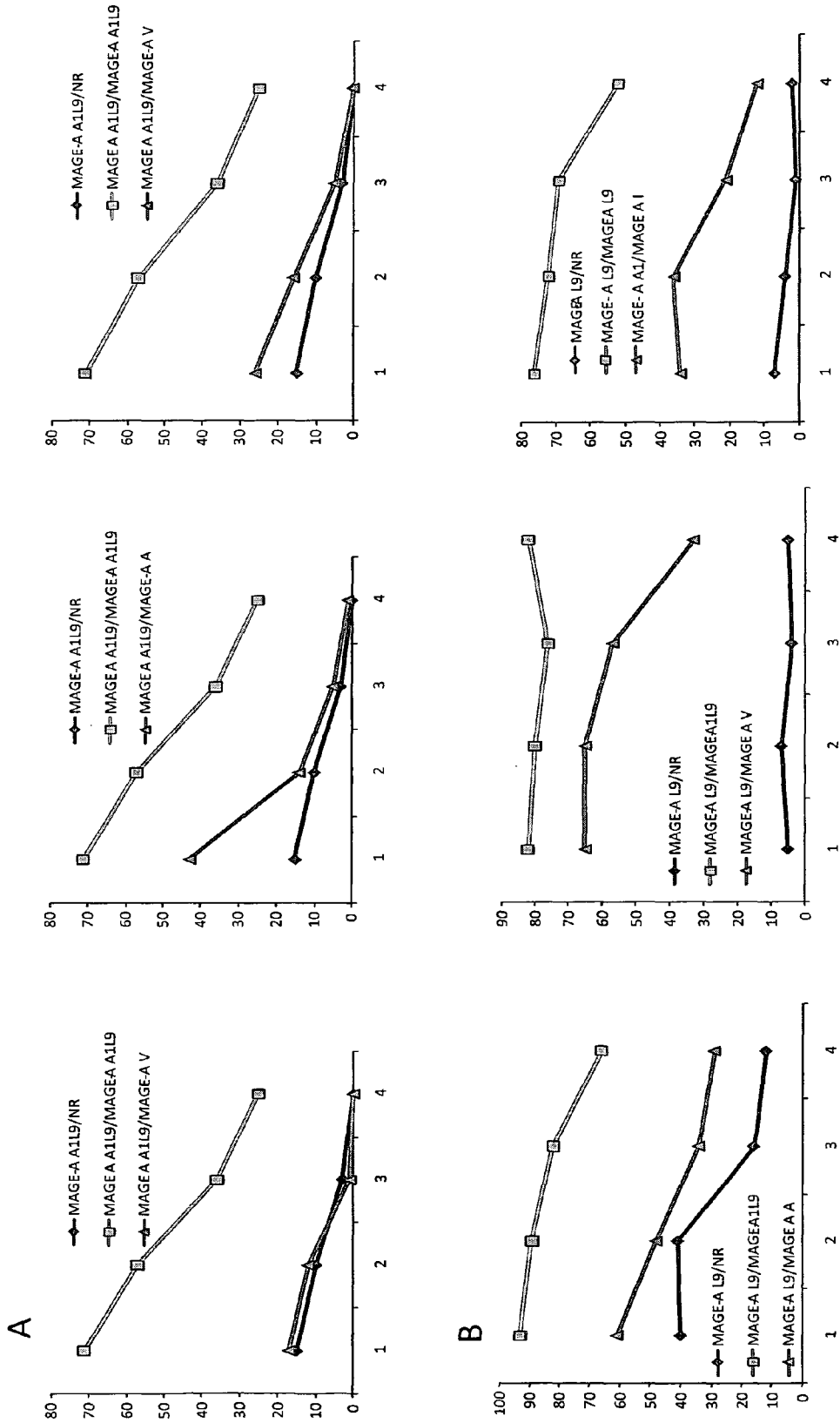

IDENTIFICATION, OPTIMIZATION AND USE OF SHARED HLA-B*0702 EPITOPES FOR IMMUNOTHERAPY

RELATED APPLICATIONS

The present application is a U.S. National Phase Application of International Application No. PCT/IB2009/006332 (filed Jun. 9, 2009) which is hereby incorporated by reference in its entirety.

SEQUENCE LISTING SUBMISSION VIA EFS-WEB

A computer readable text file, entitled "045636-5177_SequenceListing.txt," created on or about Nov. 22, 2012, with a file size of about 41 kb contains the sequence listing for this application and is hereby incorporated by reference in its entirety.

The present invention relates to the field of peptide immunotherapy. In particular, the invention provides novel methods and materials for efficiently treating patients having an HLA-B*0702 phenotype, based on peptides representing shared epitopes of tumour antigens.

Peptide immunization or immunotherapy is a therapeutic approach which is currently the subject of great interest in the context of the prevention or treatment of cancers. The principle thereof is based on immunization with peptides which reproduce T epitopes of tumour antigens that are recognized by Cytotoxic T Lymphocytes (CTLs), which play a major role in the elimination of cancer cells expressing these antigens at their surface.

It will be recalled that CTLs do not recognize whole protein antigens, but peptide fragments thereof, presented by the major histocompatibility complex (MHC) molecules expressed at the surface of various cells. These peptide fragments constitute the T epitopes. The peptides presented by the major histocompatibility complex class I (MHC I) generally have 8 to 11 amino acids, and are recognized by $CD8^+$ T cells, which represent the major component of the cytotoxic response. During the antigen processing, a peptide selection takes place, which results in a hierarchy of peptides presentation. Peptides that are preferentially presented by the MHC I molecules are called immunodominant while peptides that are weakly presented are called cryptic. Immunodominant peptides exhibit a high affinity for the MHC I and are immunogenic while cryptic peptides exhibit a low affinity for MHC I and are non-immunogenic.

The identification of tumour specific epitopes, and in particular (given the essential role of the $CD8^+$ response in cytotoxicity) of those presented by the more frequent MHC I alleles, constitutes an essential step for the development of anti-tumour immunotherapy compositions. Many tumour antigens are known at the current time; some of the T epitopes of these antigens have been identified and the effectiveness of vaccines based on peptides which reproduce these T epitopes has been shown in many cases (Menez-Jamet and Kosmatopoulos, 2009).

However, the expression of the majority of tumour antigens is restricted to certain histological types of tumours, which limits their clinical use. The search for broadly expressed "universal" tumour antigens has been intensified with the identification of antigens with functions essential for the maintenance of the oncogenic phenotype, and effort are being made to identify epitopes expressed by a majority of patients.

Another considerable limitation of peptide immunotherapy comes from the appearance, in certain patients, of tumour variants (escape variants) which no longer express the antigen recognized by the cytotoxic T lymphocytes.

Some tumour antigens belong to multigene families: within the same family, there is a sequence homology, which may result in the existence of shared epitopes common to two or more members of the same family.

Generally, various members of the same family of antigens are expressed in various tumour types; the use of an epitope shared by these antigens could make it possible to obtain anti-tumour vaccines with a broad spectrum of activity.

Furthermore, in many cases, several antigens of the same family are co-expressed in the same tumour line; since the probability of loss of the expression of all these antigens is extremely low, the use of an epitope shared by these antigens may avoid the appearance of escape variants.

Among the tumour antigens known to belong to a multigene family, mention will in particular be made of the antigens of the MAGE-A, HER, BAGE or GAGE families.

MAGE-A is a multigene family consisting of 12 homologous genes (MAGE-A1 to A12) located in the q28 region of the X chromosome (De Plaen et al., 1994). Among the members of this family, MAGE-A1, -A2, -A3, -A4, -A6, -A10 and -A12 are strongly expressed by tumours but not by normal tissues, with the exception of the testis and of the placenta.

The MAGE-A1, -A2, -A3, -A4, -A6, -A10 and -A12 antigens are present in a wide spectrum of tumours of very varied histological origin, such as melanomas, lung cancers, breast cancers, head and neck tumours, and sarcomas, myelomas, etc.

MAGE-based cancer vaccines, such as MAGE-A3 Antigen Specific Cancer Immunotherapeutic (ASCI) (GlaxoSmithKline) are currently in late phase of development with encouraging results. For example, this vaccine, which is based on tumour antigens presented to the patient's immune system as recombinant proteins in combination with a GSK proprietary adjuvant system, has completed successfully two clinical trials in melanoma and non small cell lung cancer.

The expression of each MAGE-A antigen can vary from one tumour to another, but overall, the vast majority of tumours express at least one MAGE-A antigen.

Despite the potential advantage of using shared T epitopes, this approach has only been very rarely used because of the rarity of the regions of appropriate size (at least 8 amino acids for a peptide presented by MHC I) that are completely identical from one antigen to another.

The inventors have previously described a method for identifying peptide epitopes presented by an HLA class I molecule and shared by several antigens of the same multigen family. This method is characterized by the following steps (EP1 485 719):

a) aligning the sequences of said antigens in order to identify on each of them a sequence of 8 to 10 amino acids comprising at least one common pentapeptide sequence preceded by 3 amino acids at the N-terminal end and, optionally, followed by one or two amino acids at the C-terminal end; indeed, the authors have found that an identity limited to the sequence of 5 amino acids extending from positions P4 to P8 of the peptide was sufficient.

b) preparing the peptides corresponding to the sequences identified and determining the binding affinity of each of the peptides for the HLA class I molecule concerned, and their immunogenicity using human CMH-I transgenic mice c) In case a selected peptide is cryptic and consequently non-immunogenic, the method further comprises a step of increasing its immunogenicity.

Using this method, the inventors have described an immunogenic peptide defined by the sequence YLEYRQVPV (SEQ ID No: 1), presented by HLA-A*0201 common to the MAGE-A1, -2, -3, -4, -6, -10 and -12 antigens of the MAGE-A family, capable of inducing CTLs which recognize all the MAGE-A antigens, and of lysing tumour cells expressing at least one antigen of the MAGE-A family.

Immunodominant peptides have widely been targeted by tumour vaccines in preclinical and clinical studies with disappointing results (Gross et al., 2004). Indeed, tumour antigens are frequently self proteins over-expressed by tumours and expressed at lower levels by normal cells and tissues. The immune system is unable to react against these self antigens because of the self tolerance process. Self-tolerance concerns mainly the immunodominant peptides, thus explaining the incapacity of these peptides to induce tumour immunity.

Cryptic peptides are much less involved in self tolerance process (Gross et al., 2004) and can therefore induce an efficient tumour immunity providing their immunogenicity is enhanced.

The usual strategy for enhancing the immunogenicity of cryptic peptides, which because of their low MHC I affinity are non-immunogenic, consists in increasing their affinity for the MHC I molecules via amino acids substitutions. Peptide affinity for MHC I molecules mainly depends on the presence at well defined positions (primary anchor positions) of residues called "primary anchor residues". These residues are MHC I allele specific. The presence of primary anchor residues, although often necessary, is not sufficient to ensure a high MHC I affinity. It has been shown that residues located outside the primary anchor positions (secondary anchor residues) may exert a favourable or unfavourable effect on the affinity of the peptide for the MHC I. The presence of these secondary anchor residues makes it possible to explain the existence, within the peptides having the primary anchor motifs, of a great variability in the binding affinity (Ruppert et al., 1993).

Moreover, amino acids substitutions aiming at enhancing affinity for MHC I molecule must preserve the antigenicity of such optimized peptides. CTL generated against optimized peptides must indeed cross-react with the corresponding native peptides, which are those naturally presented at the tumour cell surface.

The inventors have previously described methods for selection of cryptic peptides in tumour antigens and their optimization to induce specific immune response for patients HLA-A*0201 ((Tourdot et al., 2000), EP 1 309 860) and HLA-B*0702 (WO 2008/010098). A method for selecting HLA-A*2402-restricted cryptic epitopes has also been recently described by the inventors, in a patent application which has not been published yet. Briefly, this method consists in selecting, in an antigen, a peptide of 8 to 12 amino acids having a tyrosine in position 2, with the proviso that the peptide does not have, simultaneously, a positively charged amino acid (lysine or arginine) in position 1 and a leucine or an isoleucine or a phenylalanine in C-terminal position. Such a cryptic peptide can then be optimized by substituting its N-terminal residue with an arginine or a lysine, and/or by substituting its C-terminal residue with a leucine (or an isoleucine or a phenylalanine).

HLA-B*0702 is a frequently expressed molecule (25% of the population). Identification and optimization of HLA-B*0702 restricted tumour peptides is therefore necessary in order to develop efficient cancer vaccines for HLA-B*0702 expressing patients.

In order to identify a broad spectrum tumour vaccine for HLA-B*0702 expressing patients, the inventors have aligned the sequences of the MAGE-A antigens and searched for peptides having anchor positions 2 and 3 (respectively a proline and an arginine or a histidine or a methionine or a lysine) and an identical sequence in the region extending from positions P4 to P8 of the peptide. No corresponding sequence was found in conserved MAGE-A regions.

Sequences were then selected as having only one modification in the antigenicity region (position P4 to P8 in 9-mers, and P4 to P9 in 10-mers), and non-immunogenic epitopes were optimized as described in WO 2008/010098. Surprisingly, the inventors have demonstrated that a peptide corresponding to a cryptic HLA-B*0702 epitope modified to increase its antigenicity can raise a cytotoxic response not only against the native peptide, but also against the homologous epitope which is present on other MAGE-A antigens.

Hence, a first aspect of the present invention is a method for identifying a HLA-B*0702-restricted peptide which can trigger a cytotoxic response against at least two antigens from one single multigenic family, comprising at least the following steps:

(i) identifying, in the genes of said multigenic family, peptides of 9 or 10 amino acids having a P in position 2 and an amino acid selected in the group consisting of R, K, H and M in position 3;

(ii) aligning the sequences obtained in (i);

(iii) identifying, amongst the peptides obtained in step (i), a group of at least two peptides, in which at least one peptide is such that its antigenic region differs from those of the other peptides of the group by at most one residue, wherein said antigenic region extends from position 4 to position 8 in a peptide having 9 amino acids, and from position 4 to position 9 in a peptide having 10 amino acids.

A peptide which is such that its antigenic region differs from those of the other peptides of the group identified in step (iii) by at most one residue will be referred to hereafter as an "essentially shared peptide". Such a peptide triggers a cytotoxic response against at least two antigens from said multigenic family.

According to preferred embodiments of said method, the method enables identification of a HLA-B*0702-restricted peptide which can trigger a cytotoxic response against at least three, four, five, six, seven or more antigens from said multigenic family. This is the case when the group of peptides selected in step (iii) comprises peptides from at least three, four, five, six, seven or more genes of said multigenic family, respectively.

In a particular embodiment of the above method, the group of peptides selected in step (iii) comprises at least two peptides which have different antigenic regions. In this case, illustrated in the examples below, at least two of these peptides exhibit one and only one difference in their antigenic regions.

In a preferred embodiment, the method further comprises a step (iv) of measuring the immunogenicity of the selected essentially shared peptide. This step will be preferentially performed in vivo in an appropriate model, i.e., a model which predicts the immunogenicity of the peptide in an individual who expresses HLA-B*0702. An example of such an appropriate model is described in the experimental part and consists of a HLA-B*0702 transgenic mice. In this model, the immunogenicity of a selected peptide is measured by vaccinating the mice and testing if specific CTLs have been generated, by using human cells expressing HLA-B*0702 and loaded with the peptide as target cells. In what follows, a peptide will be considered as a non-immunogenic epitope if none of the vaccinated mice develop a specific immune response against the tested peptide. If some of the mice, but not all of them, develop a specific immune response against the tested peptide, the peptide is considered as immunogenic, but it can be advantageous to further improve its immunogenicity.

In case a selected essentially shared peptide is non-immunogenic or if its immunogenicity has to be enhanced, the method further comprises a step of increasing its immunogenicity, by a method as described in WO 2008/010098. In particular, if the selected essentially shared peptide is non-immunogenic and has any amino acid but P at its N-terminus (especially if the three first residues of said cryptic epitope are APR or APK or APH or APM), then step (v) consists of substituting the C-terminal residue of said epitope with a leucine. In case the selected essentially shared peptide is non-immunogenic and has an amino acid selected amongst L, A, I, V, M, C or T (especially L, A, I, V or M) at its C-terminus, then step (v) can be performed by substituting the N-terminal residue of said epitope with an alanine. Of course, in this method, the word "substituting" is to be understood as obtaining a peptide the sequence of which is derived from the sequence of said HLA-B*0702-restricted cryptic epitope by the mentioned substitution, whatever the technical method used to obtain said peptide. For example, the peptide can be produced by artificial peptide synthesis or by recombinant expression.

The method according to the invention can be performed for identifying epitopes which can trigger an immunogenic response against several members of any known multigenic family, such as MAGE-A, HER, BAGE or GAGE families. In a preferred embodiment, illustrated in the experimental part below, said multigenic family is the MAGE-A family.

Another aspect of the present invention is an isolated peptide identified by a method as above-described, wherein said selected peptide is selected in the group consisting of MPKTGFLII (SEQ ID No: 2), MPKTGLLII (SEQ ID No: 3), FPKTGLLII (SEQ ID No: 4), VPKTGLLII (SEQ ID No: 5), MPKAGLLII (SEQ ID No: 6), MPKTGILIL (SEQ ID No: 7), MPKTGFLIIV (SEQ ID No: 8), MPKTGFLIII (SEQ ID No: 9), MPKTGLLIIV (SEQ ID No: 10), FPKTGLLIIV (SEQ ID No: 11), VPKTGLLIIV (SEQ ID No: 12), MPKAGLLIIV (SEQ ID No: 13), MPKTGILILI (SEQ ID No: 14), GPRALAETS (SEQ ID No: 15), GPRALIETS (SEQ ID No: 16), GPRALVETS (SEQ ID No: 17), GPRALAETSY (SEQ ID No: 18), GPRALIETSY (SEQ ID No: 19), GPRALVETSY (SEQ ID No: 20), EPRKLLTQD (SEQ ID No: 21), HPRKLLTQD (SEQ ID No: 22), DPKKLLTQH (SEQ ID No: 23), DPKKLLTQY (SEQ ID No: 24), HPKKLLMQD (SEQ ID No: 25), EPRKLLTQDL (SEQ ID No: 26), EPRKLLTQDW (SEQ ID No: 27), HPRKLLTQDL (SEQ ID No: 28), HPKKLLMQDL (SEQ ID No: 29), DPKKLLTQHF (SEQ ID No: 30), DPKKLLTQYF (SEQ ID No: 31).

Of course, in the present text, the term "isolated peptide" is not to be understood narrowly. To the contrary, this term designates not only molecules in which amino acid residues (in L or D configurations) are joined by peptide (—CO—NH—) linkages, but also synthetic pseudopeptides or peptidomimetics in which the peptide bond is modified, especially to become more resistant to proteolysis, and provided their immunogenicity is not impaired by this modification.

Immunogenic optimized peptides derived from the epitopes of the above list are also part of the present invention. In what follows, the expression "optimized peptide" or "optimized immunogenic HLA-B*0702-restricted epitope" will designate an immunogenic peptide derived from a HLA-B*0702-restricted epitope (called its "cognate native peptide") by a method as described above and in WO 2008/010098. Optimized peptides according to the invention are peptides of SEQ ID Nos: 32 to 67, disclosed in Table 1 below.

TABLE 1

HLA-B7 restricted native and corresponding optimized peptides highly homologous amongst MAGE-A antigens (antigenic sequences are highlighted)

| Native peptides | | | MAGE-A corresponding | Optimized peptide | |
|---|---|---|---|---|---|
| Name | Sequence | Seq ID no | antigenic sequence | Sequence | Seq ID no |
| MAGE-A 188 (9 mers) | MPKTGFLII | 2 | MAGE A1, A6 | APKTGFLII | 32 |
|  |  |  |  | MPKTGFLIL | 33 |
|  | MPKTGLLII | 3 | MAGE A2, | APKTGLLII | 34 |
|  | FPKTGLLII | 4 | MAGE A4, | MPKTGLLIL | 35 |
|  | VPKTGLLII | 5 | MAGE A12 | FPKTGLLIL | 36 |
|  |  |  |  | VPKTGLLIL | 37 |
|  | MPKAGLLII | 6 | MAGE A3 | APKAGLLII | 38 |
|  |  |  |  | MPKAGLLIL | 39 |
|  | MPKTGILIL | 7 | MAGE A10 | APKTGILIL | 40 |
| MAGE-A 188 (10 mers) | MPKTGFLIIV | 8 | MAGE A1, | APKTGFLIIV | 41 |
|  | MPKTGFLIII | 9 | MAGE A6 | APKTGFLIII | 42 |
|  |  |  |  | MPKTGFLIIL | 43 |
|  | MPKTGLLIIV | 10 | MAGE A2, | APKTGLLIIV | 44 |
|  | FPKTGLLIIV | 11 | MAGE A4, | MPKTGLLIIL | 45 |
|  | VPKTGLLIV | 12 | MAGE A12 | FPKTGLLIIL | 46 |
|  |  |  |  | VPKTGLLIIL | 47 |
|  | MPKAGLLIIV | 13 | MAGE A3 | APKAGLLIIV | 48 |
|  |  |  |  | MPKAGLLIIL | 49 |
|  | MPKTGILILI | 14 | MAGE A10 | APKTGILILI | 50 |
|  |  |  |  | MPKTGILILL | 51 |
| MAGE-A 267 (9 mers) | GPRALAETS | 15 | MAGE A1, A4 | GPRALAETL | 52 |
|  | GPRALIETS | 16 | MAGE A2, A6 | GPRALIETL | 53 |
|  | GPRALVETS | 17 | MAGE A3, A12 | GPRALVETL | 54 |

TABLE 1-continued

HLA-B7 restricted native and corresponding optimized peptides highly
homologous amongst MAGE-A antigens (antigenic sequences are highlighted)

| | Native peptides | | MAGE-A corresponding | Optimized peptide | |
|---|---|---|---|---|---|
| Name | Sequence | Seq ID no | antigenic sequence | Sequence | Seq ID no |
| MAGE-A 267 (10 mers) | GPRALAETSY | 18 | MAGE A1, A4 | GPRALAETSL | 55 |
| | GPRALIETSY | 19 | MAGE A2, A6 | GPRALIETSL | 56 |
| | GPRALVETSY | 20 | MAGE A3, A12 | GPRALVETSL | 57 |
| MAGE-A 233 (9 mers) | EPRKLLTQD | 21 | MAGE A1, A4, A10 | EPRKLLTQL | 58 |
| | HPRKLLTQD | 22 | MAGE A12 | HPRKLLTQL | 59 |
| | DPKKLLTQH | 23 | MAGE A3 | DPKKLLTQL | 60 |
| | DPKKLLTQY | 24 | MAGE A6 | DPKKLLTQL | 61 |
| | HPKKLLMQD | 25 | MAGE A2 | HPKKLLMQL | 62 |
| MAGE-A 233 (10 mers) | EPRKLLTQDL | 26 | MAGE A1 | EPRKLLTQDL | 63 |
| | EPRKLLTQDW | 27 | MAGE A4, A10 | APRKLLTQDL | 64 |
| | HPRKLLTQDL | 28 | MAGE A12 | | |
| | HPKKLLMQDL | 29 | MAGE A2 | APKKLLMQDL | 65 |
| | DPKKLLTQHF | 30 | MAGE A3 | DPKKLLTQHL | 66 |
| | DPKKLLTQYF | 31 | MAGE A6 | DPKKLLTQYL | 67 |

Polyspecific tumour vaccination offers a broader control of tumour cells than monospecific vaccination, thereby reducing the risk of emergence of immune escape variants. In most cases, immunotherapy is then more efficient when targeting several epitopes than when targeting only one epitope, provided the tumour is known to express all targeted antigens. The inventors have previously described a polypeptide composed of HLA-A*0201 restricted optimized cryptic peptides derived from three different universal tumour antigens (TERT$_{988Y}$, HER-2/neu$_{402Y}$ and MAGE-A$_{248V9}$), named Vx-006 (WO 2007/073768). Vx-006 is able to induce a polyspecific CD8 cell response both in vivo in HLA-A*0201 transgenic HHD mice and in vitro in humans, whereas the mixture of TERT$_{988Y}$, HER-2/ne11$_{402Y}$ and MAGE-A$_{248V9}$ peptides failed to induce a trispecific response. Hence, a chimeric polypeptide comprising several epitopes can be more efficient than a mere mixture of the same epitopes to trigger a response against more than one epitope. Depending on the context, a chimeric polypeptide comprising a repetition of one single epitope can also trigger a stronger response against said epitope than a peptide consisting of said epitope. Indeed, a polypeptide organization (either with several different epitopes or with a repetition of one single epitope) can produce new junctional epitopes, especially CD4 restricted epitopes, able to optimize the targeted peptide(s)-specific immune response. Moreover, when free peptides are subcutaneously injected, peptides bind directly to MHC molecules of every cells present at the site of injection. As polypeptides need to be processed, vaccination with polypeptides is more efficient to target antigenic peptides to professional Antigenic Presenting Cells (APC) as Dendritic Cells.

A further aspect of the invention is hence a chimeric polypeptide, comprising one, two, three or more HLA-B*0702-restricted epitopes as above-described. In particular, a chimeric polypeptide according to the invention can comprise one, two, three or more native HLA-B*0702-restricted epitopes described above, or one, two, three or more immunogenic optimized HLA-B*0702-restricted epitopes selected amongst SEQ ID Nos: 32-67. Of course, optimized HLA-B*0702-restricted epitopes can also be combined, in a chimeric polypeptide, to native HLA-B*0702-restricted epitopes which have been identified as immunogenic epitopes. In a chimeric polypeptide according to the invention, the epitopes can be different from each other, and/or the same epitope can be repeated several times.

It is to be noted that when several epitopes specific for the same HLA molecule are used together, either in a mix or in a chimeric polypeptide, the epitopes are in competition for the binding to the corresponding HLA molecule. Contrarily, by using a mix of different HLA-restricted epitopes (HLA-A*0201, HLA-A*2402, HLA-B*0702 or others), or a chimeric polypeptide comprising the same different HLA-restricted epitopes, there will be no competition for HLA binding, and a polyspecific response will be obtained with certainty, provided all the HLA molecules are expressed in the vaccinated individual.

In a chimeric polypeptide according to the invention, HLA-B*0702-restricted cryptic or immunogenic (native or optimized) epitopes, described above, can hence be advantageously associated to previously described HLA-A*0201 (WO 02/02716) and/or HLA-B*0702 peptides (WO 2008/010010 and WO 2008/010098), and/or to HLA-A*2402 peptides as disclosed in Table 2 below, and/or to immunogenic epitopes derived from previously described tumour associated antigens, comprising CEA, PRAME, Tyrosinase, TRAG-3, NY-Eso-1, P53, Muc-1, PSA/PSMA, survivin, Melan-A/MART-1, TRP-1, TRP-2, WT1, EphA1, EphA2, EphA3, EphA4, G250/MN/CAIX, STEAP, alphafoetoprotein, RAGE-1, PAGE-1. Of course, a polyallelic peptides mix, comprising at least a peptide according to the present invention and one different HLA-restricted epitope (HLA-A*0201, HLA-A*2402, HLA-B*0702 or others), is also part of the present invention.

Examples of epitopes which can advantageously be combined to HLA-B*0702-restricted MAGE-A epitopes (either in a mix or in a chimeric polypeptide), as well as examples of optimized immunogenic epitopes which can advantageously be combined to (native or optimized) immunogenic HLA-B*0702-restricted MAGE-A epitopes, are described in Table 2 below. Of course, these lists are not limitative.

TABLE 2

HLA-A2, -B7 and -A24 epitopes which can be combined to HLA-B*0702-restricted MAGE-A epitopes in chimeric polypeptides according to the invention

HLA-A*0201

| | Native peptide | | | Optimized peptide | |
|---|---|---|---|---|---|
| Antigen | Sequence | No | Name | Sequence | No |
| Mart-1$_{27}$ | AAGIGILTV | 68 | Mart-1$_{27Y1}$ | YAGIGILTV | 112 |
| Mart-1$_{26}$ | EAAGIGILTV | 69 | Mart-1$_{26L27}$ | ELAGIGILTV | 113 |
| Gp100$_{177}$ | AMLGTHTMEV | 70 | Gp100$_{177Y1}$ | YMLGTHTMEV | 114 |
| Gp100$_{178}$ | MLGTHTMEV | 71 | Gp100$_{178Y1}$ | YLGTHTMEV | 115 |
| Gp100$_{154}$ | KTWGQYWQV | 72 | Gp100$_{154Y1}$ | YTWGQYWQV | 116 |
| | | | Gp100$_{154M155}$ | KMWGQYWQV | 117 |
| Gp100$_{570}$ | SLADTNSLAV | 73 | Gp100$_{570Y1}$ | YLADTNSLAV | 118 |
| Gp100$_{209}$ | TDQVPFSV | 74 | Gp100$_{209Y1}$ | YDQVPFSV | 119 |
| | | | Gp100$_{209M210}$ | YMQVPFSV | 120 |
| Gp100$_{476}$ | VLYRYGSFSV | 75 | Gp100$_{476Y1}$ | YLYRYGSFSV | 121 |
| Gp100$_{457}$ | LLDGTATLRL | 76 | Gp100$_{457Y1}$ | YLDGTATLRL | 122 |
| HER-2/neu$_{799}$ | QLMPYGCLL | 77 | HER-2/neu$_{799Y1}$ | YLMPYGCLL | 123 |
| HER-2/neu$_{369}$ | KIFGSLAFL | 78 | HER-2/neu$_{369Y1}$ | YIFGSLAFL | 124 |
| HER-2/neu$_{789}$ | CLTSTVQLV | 79 | HER-2/neu$_{789Y1}$ | YLTSTVQLV | 125 |
| HER-2/neu$_{48}$ | HLYQGCQW | 80 | HER-2/neu$_{48Y1}$ | YLYQGCQW | 126 |
| HER-2/neu$_{773}$ | VMAGVGSPYV | 81 | HER-2/neu$_{773Y1}$ | YMAGVGSPYV | 127 |
| HER-2/neu$_{5}$ | ALCRWGLL | 82 | HER-2/neu$_{5Y1}$ | YLCRWGLL | 128 |
| HER-2/neu$_{851}$ | VLVKSPNHV | 83 | HER-2/neu$_{851Y1}$ | YLVKSPNHV | 129 |
| HER-2/neu$_{661}$ | ILLVVVLGV | 84 | HER-2/neu$_{661Y1}$ | YLLVVVLGV | 130 |
| HER-2/neu$_{650}$ | PLTSIISAV | 85 | HER-2/neu$_{650Y1}$ | YLTSIISAV | 131 |
| HER-2/neu$_{466}$ | ALIHHNTHL | 86 | HER-2/neu$_{466Y1}$ | YLIHHNTHL | 132 |
| HER-2/neu$_{402}$ | TLEEITGYL | 87 | HER-2/neu$_{402Y1}$ | YLEEITGYL | 133 |
| HER-2/neu$_{391}$ | PLQPEQLQV | 88 | HER-2/neu$_{391Y1}$ | YLQPEQLQV | 134 |
| HER-2/neu$_{971}$ | ELVSEFSRM | 89 | HER-2/neu$_{971Y1}$ | YLVSEFSRM | 135 |
| EphA2$_{61}$ | DMPIYMYSV | 90 | EphA2$_{61Y1}$ | YMPIYMYSV | 136 |
| HER2$_{911}$ | TVWELMTFGA | 91 | HER$_{911Y1V10}$ | YVWELMTFGV | 137 |
| HER4$_{911}$ | TIWELMTFGG | 92 | | | |
| HER1$_{911}$ | TVWELMTFGS | 93 | | | |
| HER2$_{722}$ | KVKVLGSGA | 94 | HER$_{722Y1V9}$ | YVKVLGSGV | 138 |
| HER3$_{722}$ | KLKVLGSGV | 95 | | | |
| HER4$_{722}$ | RVKVLGSGA | 96 | | | |
| HER1$_{722}$ | KIKVLGSGA | 97 | | | |
| HER2$_{845}$ | DLAARNVLV | 98 | HER$_{845Y1}$ | YLAARNVLV | 139 |
| HER3$_{845}$ | NLAARNVLL | 99 | | | |
| HER2$_{904}$ | DVWSYGVTV | 100 | HER$_{904Y1}$ | YVWSYGVTV | 140 |
| HER4$_{904}$ | DVWSYGVTI | 101 | | | |
| HER2$_{933}$ | DLLEKGERL | 102 | HER$_{933Y1}$ | YLLEKGERL | 141 |
| HER1$_{933}$ | SILELKGERL | 103 | | | |
| HER2$_{945}$ | PICTIDVYMI | 104 | HER$_{945Y1}$ | YICTIDVYMV | 142 |
| HER3$_{945}$ | QICTIDVYMV | 105 | | | |
| HER4$_{945}$ | PICTIDVYMV | 106 | | | |
| HER1$_{945}$ | PICTIDVYKI | 107 | | | |
| MAGE-A$_{248G9}$ | YLEYRQVPG | 108 | MAGE-A$_{248V9}$ | YLEYRQVPV | 143 |
| MAGE-A$_{248D9}$ | YLEYRQVPD | 109 | | | |
| TERT$_{988}$ | DKQVBSKQTV | 110 | TERT$_{988Y1}$ | YLQVNSLQTV | 144 |
| TERT$_{572}$ | RLFFYRKSV | 111 | TERT$_{572Y1}$ | YLFFYRKSV | 145 |

HLA-B*0702

| Native peptide | | | Optimized peptide | | |
|---|---|---|---|---|---|
| Name | Sequence | No | Name | Sequence | No |
| TERT$_{444}$ | DPRRLVQLL | 146 | TERT$_{444A1}$ | APRRLVQLL | 151 |
| CEA$_{188/554}$ | SPRLQLSNG | 147 | CEA$_{188/554L9}$ | SPRLQLSNL | 152 |
| HER-2/neu$_{1069}$ | APRSPLAPS | 148 | HER-2/neu$_{1069L9}$ | APRSPLAPL | 153 |
| HER-2/neu$_{760}$ | SPKANKEIL | 149 | HER-2/neu$_{760A1}$ | APKANKEIL | 154 |
| HER-2/neu$_{246}$ | GPKHSDCLA | 150 | HER-2/neu$_{246A1}$ | APKHSDCLA | 155 |

HLA-A*2402

| Native peptide | | | Optimized peptide | | |
|---|---|---|---|---|---|
| Name | Sequence | No | Name | Sequence | No |
| TERT 403 | PYGVLLKTH | 156 | TERT 403 $_{KIL9}$ | KYGVLLKTL | 165 |
| TERT 770 | PYMRQFVAH | 157 | TERT 770 $_{RIL9}$ | RYMRQFVAL | 166 |
| HER 780 | PYVSRLLGI | 158 | HER 780 $_{R1}$ | RYVSRLLGI | 167 |
| EphA2 47 | PYGKGWDLM | 159 | EphA2 47 $_{RIL9}$ | RYGKGWDLL | 168 |
| EphA2 502 | TYLVQVQAL | 160 | EphA2 502 $_{R1}$ | RYLVQVQAL | 169 |
| EphA2 817 | PYWELSNHE | 161 | EphA2 817 $_{RIL9}$ | RYWELSNHL | 170 |
| Her2/neu 922 | PYDGIPARE | 162 | | | |
| MAGE 261 | RYEFLWGPR | 163 | | | |
| Her2/neu 300 | PYNYLSTDV | 164 | | | |

The skilled artisan can chose any known technique to produce such polypeptides. For example, the polypeptide can be obtained by chemical synthesis, or by using the technology of genetic engineering (Velders et al., 2001).

Another object of the present invention is an isolated nucleic acid molecule designed to cause the expression of a cryptic HLA-B*0702-restricted MAGE-A epitope, or of an immunogenic HLA-B*0702-restricted MAGE-A epitope (either native or optimized), or of a chimeric polypeptide as above-described. By "designed to cause the expression of" a peptide is herein meant that said peptide is expressed as such, isolated from the whole antigen from which its sequence has been selected (and, in appropriate cases, optimized as above-described), when the nucleic acid is introduced in an appropriate cell. The region encoding the epitope or chimeric polypeptide will typically be situated in the polynucleotide under control of a suitable promoter. Bacterial promoters will be preferred for expression in bacteria, which can produce the polypeptide either in vitro, or, in particular circumstances, in vivo. An example of bacterium that can be used to produce a peptide or polypeptide according to the invention, directly in vivo, is *Listeria monocytogenes*, which is a facultative intracellular bacterium that enters professional antigen-presenting cells by active phagocytosis (Paterson and Maciag, 2005). Alternatively, a nucleic acid according to the invention can be administered directly, using an appropriate vector. In this case, a tissue-specific, a strong constitutive, or an endogenous promoter can be used to control the peptide expression. Suitable vector systems include naked DNA plasmids, liposomal compositions to enhance delivery, and viral vectors that cause transient expression. Examples of viral vectors are adenovirus or vaccinia virus vectors and vectors of the herpes family, especially in a non-replicative form.

The present invention also pertains to a pharmaceutical composition comprising at least, as an active principle, a HLA-B*0702-restricted MAGE-A cryptic epitope as above-described, or an immunogenic (optimized or native) HLA-B*0702-restricted MAGE-A epitope as mentioned above, or a chimeric polypeptide according to the invention, or a nucleic acid encoding any of these, and/or a vector carrying said nucleic acid. Formulation of pharmaceutical compositions will accord with contemporary standards and techniques. Medicines intended for human administration will be prepared in adequately sterile conditions, in which the active ingredient(s) are combined with an isotonic solution or other pharmaceutical carrier appropriate for the recommended therapeutic use. Suitable formulations and techniques are generally described in the latest edition of Remington's Pharmaceutical Sciences (Maack Publishing Co, Easton Pa.).

In particular, a HLA-B*0702-restricted MAGE-A epitope or a chimeric polypeptide or a nucleic acid according to the invention can be used for the preparation of a composition for preventive or curative anti-cancer immunotherapy. The peptide GPRALVETL (SEQ ID No: 54), and chimeric polypeptides comprising it, are especially suited for this purpose.

In a particular embodiment, a pharmaceutical composition according to the invention is a vaccine. In this latter case, the components described above can be combined with an adjuvant to potentiate the immune response. Classic adjuvants include oil emulsions, like Incomplete Freund's Adjuvant or Montanide, and adherent surfaces such as alum. Adjuvants that recruit and activate dendritic cells particularly via TLR (such as bacterial DNA or bacterial membrane derived proteins) or help elicit cytotoxic T cells are especially useful. Other factors that otherwise boost the immune response or promote apoptosis or elimination of cancer cells can also be included in the composition, such as IL-2 or IL-12 cytokines or GM-CSF.

Multiple doses and/or different combinations of the immunogenic compositions of this invention can be packaged for distribution separately or together. Each composition or set of compositions, such as the kits of parts described below, can be accompanied with written instructions regarding the use of the composition or combination for eliciting an immune response and/or for the treatment of cancer.

In a previous patent application (WO 2006/120038), the Applicant has described a vaccination protocol which enables the initiation and maintenance of a T cell response targeting sub-dominant/cryptic epitopes. The results reported in WO 2006/120038 demonstrate that injection of a native peptide corresponding to a sub-dominant/cryptic epitope, following vaccination with its cognate optimized peptide, can maintain the immune response initiated by said optimized peptide.

According to the invention, a HLA-B*0702-restricted MAGE-A cryptic epitope can hence be used for the preparation of a medicinal composition for maintaining the CTL immune response initiated by its cognate optimized peptide. An immunogenic peptide having an optimized immunogenic HLA-B*0702-restricted MAGE-A epitope sequence derived from a HLA-B*0702-restricted MAGE-A cryptic epitope can also be used, for the preparation of a medicinal composition for initiating a CTL immune response against said HLA-B*0702-restricted MAGE-A cryptic epitope, but also against all the epitopes of the group selected in step (iii) of the above-described method. Of course, mix of peptides from the group selected in step (iii) can also be used for maintaining the CTL immune response initiated by the essentially shared peptide. For example, a mix of peptides SEQ ID No: 15-17 can be used for maintaining the CTL immune response initiated by the peptide of SEQ ID No: 54.

The present invention also encompasses a method for vaccinating a patient against a tumoral or viral antigen, wherein said method comprises a first step of vaccination with an optimized immunogenic peptide cognate to a native HLA-B*0702-restricted MAGE-A cryptic epitope of said antigen or epitopes of the group selected in step (iii), followed by a second step of vaccination with said native peptide or mix of peptides of the considered group.

In such a method, the first step and/or the second step can be performed by using a chimeric polypeptide comprising one, two, three or more optimized or cryptic peptides as above-described, instead of single-epitope peptides. In particular, a chimeric polypeptide comprising several cryptic epitopes having at most one variant position in their antigenic region, can be used to maintain the CTL immune response initiated by optimized peptide cognate to one of said cryptic epitopes. For example, a chimeric polypeptide comprising the sequences SEQ ID No: 15-17 can be used for maintaining the CTL immune response initiated by the peptide of SEQ ID No:54. It is to be noted that due to the expression tropism of MAGE-A antigens, if a HLA-B*0702-restricted epitope as described above proves to be immunogenic, the same native immunogenic epitope can be used in both vaccination steps. In particular, a native immunogenic MAGE-A epitope can advantageously be combined with native cryptic epitopes in a first chimeric polypeptide or mix of mono-epitope peptides, and with optimized epitopes, in a second chimeric polypeptide or mix of mono-epitope peptides.

The invention also pertains to a kit of parts comprising, in separate formulations or containers (vials, tubes, etc.):

(i) a first peptide comprising a sequence of a HLA-B*0702-restricted MAGE-A native (preferably cryptic) epitope, and (ii) a second peptide comprising a sequence corresponding to an optimized immunogenic epitope cognate to the native epitope recited in (i).

Examples of peptides which can be part of a kit according to the invention are the peptides of SEQ ID Nos: 2 to 31 which can constitute the first peptide, the second peptide being then derived from said first peptide by a method for increasing its immunogenicity, as described above and in WO 2008/010098. A preferred kit according to the invention comprises the peptide of SEQ ID No: 54 and, in another container, the peptide of SEQ ID No: 17 or 15 or 16, preferentially the peptide of SEQ ID No: 17. In a variant of this kit, the kit also comprises peptides of SEQ ID Nos: 16 and/or 15, either in the same container as SEQ ID No: 17, or in one or several separate container(s).

Other kits of parts according to the invention comprise at least one chimeric polypeptide. In this embodiment, the kit also comprises at least a peptide cognate to one of the epitopes comprised in the chimeric polypeptide, wherein said cognate peptide is either isolated or included in another chimeric polypeptide.

Several preferred variants of such kits are contemplated: in a first embodiment, the kit comprises, in separate formulations, a first chimeric polypeptide comprising one, two, three or more HLA-B*0702-restricted MAGE-A cryptic epitopes, and a second chimeric polypeptide corresponding to its cognate HLA-B*0702-restricted MAGE-A immunogenic chimeric polypeptide (which means that it comprises optimized HLA-B*0702-restricted MAGE-A immunogenic epitopes cognate to the cryptic epitopes comprised in the first chimeric polypeptide). In a second embodiment, the kit comprises one, two, three or more peptides corresponding to distinct HLA-B*0702-restricted MAGE-A cryptic epitopes, wherein said peptides are either mixed in one single formulation, or separated in several formulations and, in a separate formulation, a chimeric polypeptide comprising the optimized HLA-B*0702-restricted MAGE-A immunogenic epitopes cognate to said cryptic peptides.

As mentioned above, a polyallelic stimulation (i.e., using epitopes specific for different HLA molecules) can advantageously be performed to obtain a polyspecific response. Accordingly, preferred embodiments of the kits according to the invention comprise, in separate containers:

(i) a polyallelic peptides mix or a polyallelic chimeric polypeptide, comprising at least a HLA-B*0702-restricted MAGE-A native (preferably cryptic) epitope as described above and at least one different HLA-restricted native (preferably cryptic) epitope (from and antigen of the MAGE-A family or from another antigen), and (ii) a polyallelic peptides mix or a polyallelic chimeric polypeptide, comprising at least a HLA-B*0702-restricted MAGE-A immunogenic epitope cognate to the HLA-B*0702-restricted MAGE-A native epitope recited in (i), and at least another immunogenic epitope cognate to the other native epitope recited in (i).

Alternatively, the kits according to the invention can comprise, instead of at least part the peptides or chimeric polypeptides, nucleic acid(s) encoding said peptides or chimeric polypeptides. In this case, the nucleic acid(s) is(are) as above-described.

In the following description of some specific kits according to the invention, mention will be made only of the peptides (native or optimized) included therein; it is understood that chimeric polypeptide(s) (comprising native cryptic epitopes or optimized epitopes) can be enclosed in the kits instead of single-epitope peptides, and that nucleic acid(s) can also be included in addition or instead of at least part of said peptides or chimeric polypeptides.

In a particular embodiment of the invention, the kit is a vaccination kit, wherein said first (native) and second (cognate optimized) peptides are in separate vaccination doses. In a preferred embodiment, the vaccination kit comprises 2 or 3 doses of optimized peptide, and 3, 4, 5 or 6 doses of native peptide. A particular vaccination kit according to the invention is adapted for the first vaccination sequence of 6 injections, and comprises 2 or 3 doses of optimized peptide, and 4 or 3 doses of native peptide. In case of long-lasting diseases, it is preferable to maintain the level of immunity obtained after this primo-vaccination, by regular recalls. This can be done, for example, by injections performed every 1 to 6 months. Therefore, complementary kits, comprising at least 2 doses, and up to 40 or 50 doses of native peptide, are also part of the present invention. Alternatively, the vaccination kit can comprise 2 to 3 doses of optimized peptide, and 3 to 40 or up to 50 doses of native peptide. Of course, said native and optimized peptides present in the kit are as described above.

Each dose comprises between 0.1 and 10 mg of peptide, preferably from 1 to 5 mg, or between 1 and 20 mg of polypeptide. In a preferred embodiment, each dose is formulated for subcutaneous injection. For example, each dose can be formulated in 0.3 to 1.5 ml of an emulsion of aqueous solution emulsified with Montanide ISA51, used as an adjuvant. The skilled artisan can choose any other adjuvant(s) in place of (or in addition to) Montanide ISA51. In a particular embodiment, the doses are in the form of an aqueous solution. Alternatively, the doses can be in the form of a lyophilized peptide, for extemporaneous preparation of the liquid solution to be injected. Other possible components of said kits are one or several adjuvants, to be added to the peptide compositions before administration, and a notice describing how to use said kits.

The invention is further illustrated by the following figures and examples.

LEGENDS OF FIGURES

Figure 1:
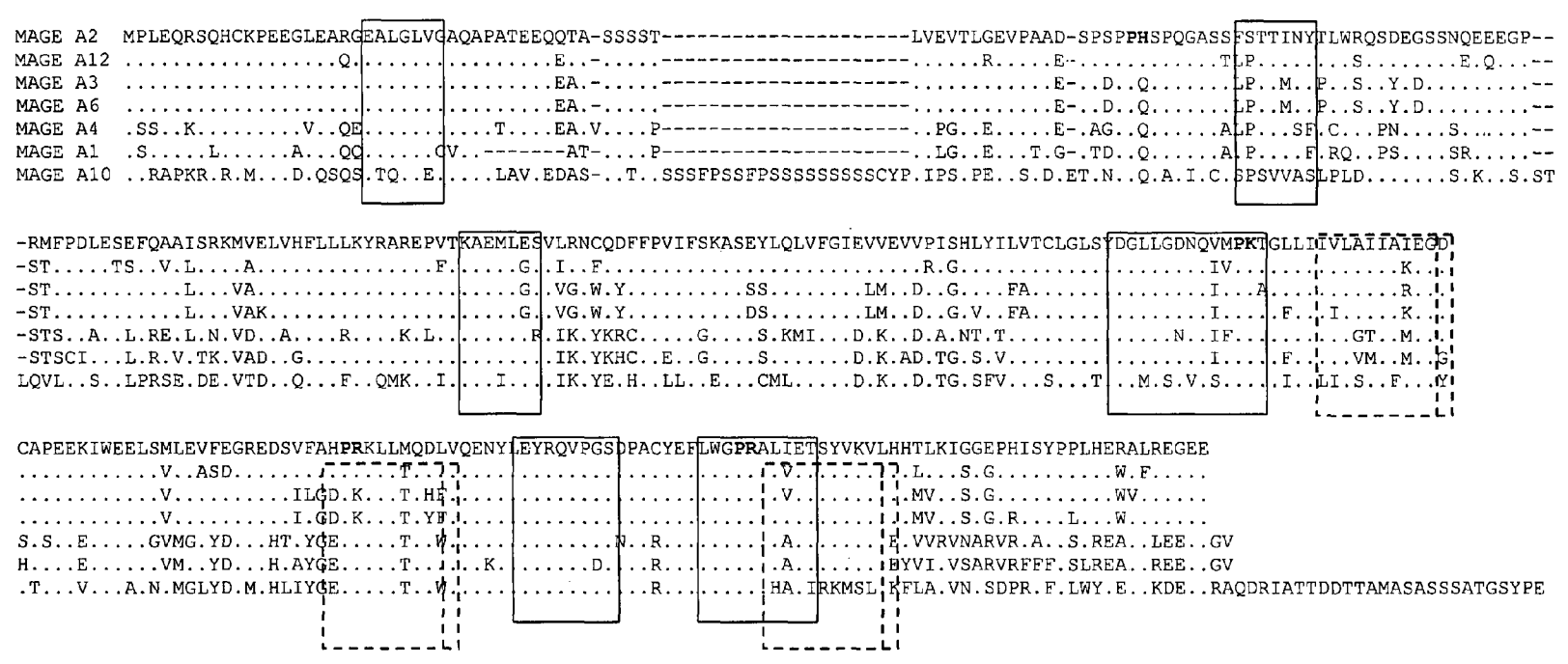

FIG. 1: MAGE-A multigene family sequences. In order to identify one or more epitopes shared by the various MAGE-A antigens (SEQ ID NO: 174-180) and presented by the HLA-B*0702 molecule, the sequences of the MAGE-A antigens were aligned, and regions of at least 5 amino acids were selected on the basis of their homology between these antigens (boxed in black continuous line). Amino acids that are completely identical from MAGE-A1 (SEQ ID NO: 174), -A2 (SEQ ID NO: 175), -A3 (SEQ ID NO: 176), -A4 (SEQ ID NO: 177), -A6 (SEQ ID NO: 178), -A12 (SEQ ID NO: 179) and/or A10 (SEQ ID NO: 180) are highlighted in grey.

FIG. 2: Immunogenicity of HLA-B*0702 restricted optimized cryptic peptides. HLA-B*0702 transgenic mice were vaccinated with the optimized peptides following the described protocol and generated CTL were tested against T2-B7 targets loaded with the optimized and both corresponding native peptides as indicated. A; Vaccination with the MAGE-A A1L9 peptide of SEQ ID No:171, B; Vaccination with the monomodified MAGE A L9 peptide of SEQ ID No: 54.

EXAMPLES

The examples have been performed using the following materials and methods:

Transgenic Mice.

The HLA-B7 H-2 class-I knockout mice were previously described (Rohrlich et al., 2003).

Cells.

HLA-B*0702 transfected human T2-B7 cells were previously described (Rohrlich et al., 2003).

Peptides and Plasmids.

Peptides were synthesized by Epytop (Nimes, France). HLA-B*0702 plasmid was provided by Dr. Lemonnier (Institut Pasteur, Paris, France) (Rohrlich et al., 2003).

Measurement of Peptide Relative Affinity to HLA-B*0702.

The protocol used has been described previously (Rohrlich et al., 2003). Briefly, T2-B7 cells were incubated at 37° C. for 16 hours with peptides concentrations ranging from 100 µM to 0.1 µM, and then stained with ME-1 monoclonal antibody (mAb) to quantify the surface expression of HLA-B*0702. For each peptide concentration, the HLA-B*0702 specific staining was calculated as the percentage of staining obtained with 100 µM of the reference peptide $CMV_{265-274}$ (R10V; RPHERNGFTV, SEQ ID NO: 172). The relative affinity (RA) was determined as: RA= (Concentration of each peptide that induces 20% of HLA-B*0702-expression/Concentration of the reference peptide that induces 20% of HLA-B*0702 expression).

CTL Induction In Vivo in HLA-B*0702 Transgenic Mice.

Mice were injected subcutaneously with 100 µg of peptide emulsified in Incomplete Freund's Adjuvant (IFA) in the presence of 150 µg of the $I-A^b$ restricted $HBVcore_{128}$ T helper epitope (TPPAYRPPNAPIL, SEQ ID NO: 173). After 11 days, 5×10⁷ spleen cells were stimulated in vitro with peptide (10 µM). On day 6 of culture, the bulk responder populations were tested for specific cytotoxicity.

Cytotoxic Assay.

Targets were labelled with 100 µCi of $Cr^{51}$ for 60 min, plated in 96-well V-bottomed plates (3×10³ cell/well in 100 µL of RPMI 1640 medium) and, when necessary, pulsed with peptides (1 µM) at 37° C. for 2 hours. Effectors were then added in the wells and incubated at 37° C. for 4 hours. Percentage of specific lysis was determined as: % Lysis= (Experimental Release−Spontaneous Release)/(Maximal Release−Spontaneous Release)×100.

Example 1: Identification of Cryptic Epitopes Presented by the HLA-B*0702 Molecule that are Shared by the Mage-A1, -A2, -A3, -A4, -A6, -A12 and/or -A10 Antigens, and Determination of their Affinities with Said HLA Molecule In order to identify one or more epitopes shared by the various MAGE-A antigens and presented by the HLA-B*0702 molecule, the sequences of the MAGE-A antigens were aligned (FIG. 1), and regions of 9 to 10 amino acids were searched on the basis of their homology between MAGE-A1, -A2, -A3, -A4, -A6, -A12 and/or -A10 antigens (sequences highlighted in grey, FIG. 1). As MAGE-A10 sequence is less homologous to MAGE-A1, -A2, -A3, -A4, -A6, -A12, shared sequences were not eliminated if no equivalent was found in MAGE-A10 (FIG. 1).

In the following description, these regions of 9 to 10 amino acids are denoted with reference to the position of their first amino acid in the MAGE-A1 sequence. Only two regions of at least 9 amino acids were identified (position 181 and 270). As previously described, as few homologous sequences exist, authors described a method to identify a sequence of 8 to 10 amino acids comprising at least one common pentapeptide sequence preceded by 3 amino acids at the N-terminal end and, optionally, followed by one or two amino acids at the C-terminal end; indeed, the authors have found that an identity limited to the sequence of 5 amino acids extending from positions P4 to P8 of the peptide was sufficient. Sequences of at least 5 common amino acids are boxed in FIG. 1. Using this method of selection, four additional regions were indentified (position 21, 65, 132, 256).

Peptides of 9 or 10 amino acids having a P in position 2 and an amino acid selected in the group consisting of R, K, H and M in position 3 corresponding to HLA-B*0702 restricted peptides were then identified. As shown in FIG. 1, no sequence completely identical was found.

In order to broaden the choice of the candidate peptides, a second search was carried out, according to the described method, to select regions exhibiting complete sequence identity between positions P4 and P8. One more time, no sequence was indentified. Finally, a third search was performed, to select sequences having only one mismatch between positions P4 and P8. Identified sequences are in table 1 above, and are boxed in dotted line in FIG. 1.

The MAGE-A269 (9 mers) group was selected as only three different sequences allow recognizing all the MAGE-A genes (accept MAGE-A10). This group comprises three peptides: MAGE-A A, SEQ ID No15 (MAGE-A1, -A4), MAGE-A I, SEQ ID No16 (MAGE-A2, -A6) and MAGE-A V, SEQ ID No17 (MAGE-A3, -A12), which differ in terms of their position P6. No corresponding sequence was found in MAGE-A10.

Each peptide was tested for its capacity to bind HLA-B*0702 (table 3).

TABLE 3

Affinity of the selected cryptic peptides to HLA-B*0702.

| Peptide | Sequence | RA | SEQ ID No |
|---|---|---|---|
| MAGE-A A | GPRALAETS | − | 15 |
| MAGE-A I | GPRALIETS | − | 16 |
| MAGE-A V | GPRALVETS | − | 17 |

RA = Relative Affinity = (Concentration of each peptide that induces 20% of HLA-B*0702-expression/Concentration of the reference peptide that induces 20% of HLA-B*0702 expression), (−) means RA > 10, (+/−) 1 < RA < 10, (+) 5 < RA < 10, (++) RA < 1

None of the three native peptides was shown to bind to HLA-B*0702 molecules, despite the fact that these peptides harbour primary P2R3 anchor positions, showing that they are cryptic peptides. The aim of this study was to find an immunogenic peptide that is capable to induce a specific immune response able to recognize a cell whatever the MAGE-A gene expressed. More precisely, CTL induced by the vaccination with the validated peptide, have to be able to recognize a cell which expresses or presents both MAGE-A A, MAGE-A I and MAGE-A V cryptic native peptide (native peptide cross recognition). Selected peptides were then modified to enhance their immunogenicity.

Example 2: Enhancement of the Immunogenicity of the Selected Peptide

To enhance HLA-B*0702 affinity and consequently immunogenicity of these low affinity peptides, it is necessary to identify unfavourable secondary anchor motifs and substitute them with favourable motifs. Native peptides were selected to have the P2R3 primary anchor positions; the interest was then focused on secondary anchor position 1 and 9.

The first optimized peptide tested was based on the MAGE-A V sequence, modified at both positions respectively by replacing the P1 by an alanine (A) and the P9 by a leucine (L), known to be amino acids favourable for HLA-B*0702 binding.

The peptide MAGE-A A1L9 has the sequence APRALVETL (SEQ ID n° 171), and was able to bind to MHC (Table 4), confirming that modifications have enhanced its affinity for HLA-B*0702 molecules. HLA-B*0702 transgenic mice were then vaccinated with the modified peptide, and eleven days later, their spleen cells were in vitro stimulated with the peptide. As shown in FIG. 2A and table 4, the modified peptide was immunogenic but MAGE-A A1L9 specific CTLs induced were not able to cross-recognize the native peptides.

The substitutions should however preserve the conformation of the peptide segment that interacts with the TCR, preserving the peptide specificity. As two modifications could modify dramatically the peptide conformation, a new optimized peptide was tested, only modified at position 9. Indeed, a G at position 1 is described as neutral and non unfavourable for the peptide affinity to MHC.

MAGE-A L9 (SEQ ID No: 54) was shown to be strongly immunogenic, as all vaccinated mice developed a specific immune response against the MAGE-A L9. Most importantly, CTLs induced by the MAGE-A L9 peptide were able to recognize a target cell loaded with each of the native cryptic peptides (FIG. 2B and table 4).

TABLE 4 affinity and immunogenicity of the optimized peptides.

| Peptide | Sequence | RA | Immunogenicity | Native peptide cross recognition | SEQ ID No |
|---|---|---|---|---|---|
| MAGE-A A | GPRALAETS | − | | | 15 |
| MAGE-A I | GPRALIETS | − | | | 16 |
| MAGE-A V | GPRALVETS | − | | | 17 |
| MAGE-A A1L9 | APRALVETL | + | 6/11 | MAGE-A A (1/8)<br>MAGE-A I (0/3)<br>MAGE-A V (0/3) | 171 |
| MAGE-A L9 | GPRALVETL | ND | 18/18 | MAGE-A A (3/8)<br>MAGE-A I (3/5)<br>MAGE-A V (4/5) | 54 |

RA = Relative Affinity = (Concentration of each peptide that induces 20% of HLA-B*0702-expression/Concentration of the reference peptide that induces 20% of HLA-B*0702 expression), (−) means RA > 10, (+/−) 1 < RA < 10, (+) 5 < RA < 10, (++) RA < 1
(X/Y) means that X mice developed a specific response for a total of Y mice vaccinated.

REFERENCES

De Plaen, E., Arden, K., Traversari, C., Gaforio, J. J., Szikora, J. P., De Smet, C., Brasseur, F., van der Bruggen, P., Lethe, B., Lurquin, C. and et al. (1994) Structure, chromosomal localization, and expression of 12 genes of the MAGE family. *Immunogenetics*, 40, 360-369.

Gross, D. A., Graff-Dubois, S., Opolon, P., Cornet, S., Alves, P., Bennaceur-Griscelli, A., Faure, O., Guillaume, P., Firat, H., Chouaib, S., Lemonnier, F. A., Davoust, J., Miconnet, I., Vonderheide, R. H. and Kosmatopoulos, K. (2004) High vaccination efficiency of low-affinity epitopes in antitumor immunotherapy. *J Clin Invest*, 113, 425-433.

Menez-Jamet, J. and Kosmatopoulos, K. (2009) Development of optimized cryptic peptides for immunotherapy. *IDrugs*, 12, 98-102.

Paterson, Y. and Maciag, P. C. (2005) Listeria-based vaccines for cancer treatment. *Curr Opin Mol Ther*, 7, 454-460.

Rohrlich, P. S., Cardinaud, S., Firat, H., Lamari, M., Briand, P., Escriou, N. and Lemonnier, F. A. (2003) HLA-B*0702 transgenic, H-2 KbDb double-knockout mice: phenotypical and functional characterization in response to influenza virus. *Int Immunol*, 15, 765-772.

Ruppert, J., Sidney, J., Celis, E., Kubo, R. T., Grey, H. M. and Sette, A. (1993) Prominent role of secondary anchor residues in peptide binding to HLA-A2.1 molecules. *Cell*, 74, 929-937.

Tourdot, S., Scardino, A., Saloustrou, E., Gross, D. A., Pascolo, S., Cordopatis, P., Lemonnier, F. A. and Kosmatopoulos, K. (2000) A general strategy to enhance immunogenicity of low-affinity HLA-A2. 1-associated peptides: implication in the identification of cryptic tumor epitopes. *Eur J Immunol*, 30, 3411-3421.

Velders, M. P., Weijzen, S., Eiben, G. L., Elmishad, A. G., Kloetzel, P. M., Higgins, T., Ciccarelli, R. B., Evans, M., Man, S., Smith, L. and Kast, W. M. (2001) Defined flanking spacers and enhanced proteolysis is essential for eradication of established tumors by an epitope string DNA vaccine. *J Immunol*, 166, 5366-5373.

The invention claimed is:

1. An isolated peptide consisting of a HLA-B*0702-restricted epitope selected from the group consisting of SEQ ID NO:52 to 54.

2. A chimeric polypeptide, comprising two or more HLA-B*0702-restricted epitopes selected from the group consisting of SEQ ID NO:32-67.

3. A composition comprising at least, as an active ingredient, the isolated peptide according to claim 1, or the chimeric polypeptide according to claim 2, and further comprising a pharmaceutical carrier.

4. A kit of parts comprising, in separate containers:
   (i) a first peptide comprising a HLA-B*0702-restricted epitope, wherein said first peptide is a chimeric polypeptide comprising two or more HLA-B*0702-restricted epitopes selected from the group consisting of SEQ ID NO: 2 to 31, and
   (ii) a second peptide consisting of the chimeric polypeptide of claim 2.

5. The kit according to claim 4, wherein said first peptide comprises a sequence selected from the group consisting of SEQ ID NO: 15, SEQ ID NO: 16 and SEQ ID NO: 17, and said second peptide comprises the sequence of SEQ ID NO: 54.

6. The kit according to claim 4, which is a vaccination kit, wherein said first and second peptides are in separate vaccination doses.

7. The isolated peptide according claim 1, wherein the HLA-B*0702-restricted epitope consists of the sequence of SEQ ID NO: 52.

8. The isolated peptide according to claim 1, wherein the HLA-B*0702-restricted epitope consists of the sequence of SEQ ID NO: 53.

9. The isolated peptide according to claim 1, wherein the HLA-B*0702-restricted epitope consists of the sequence of SEQ ID NO: 54.

* * * * *

SEQUENCE LISTING

```
<160> NUMBER OF SEQ ID NOS: 180

<210> SEQ ID NO 1
<211> LENGTH: 9
<212> TYPE: PRT
<213> ORGANISM: Artificial
<220> FEATURE:
<223> OTHER INFORMATION: Immunogenic peptide presented by HLA-A0201

<400> SEQUENCE: 1

Tyr Leu Glu Tyr Arg Gln Val Pro Val
1               5

<210> SEQ ID NO 2
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 2
```

```
Met Pro Lys Thr Gly Phe Leu Ile Ile
1               5

<210> SEQ ID NO 3
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 3

Met Pro Lys Thr Gly Leu Leu Ile Ile
1               5

<210> SEQ ID NO 4
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 4

Phe Pro Lys Thr Gly Leu Leu Ile Ile
1               5

<210> SEQ ID NO 5
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 5

Val Pro Lys Thr Gly Leu Leu Ile Ile
1               5

<210> SEQ ID NO 6
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 6

Met Pro Lys Ala Gly Leu Leu Ile Ile
1               5

<210> SEQ ID NO 7
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 7

Met Pro Lys Thr Gly Ile Leu Ile Leu
1               5

<210> SEQ ID NO 8
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 8
```

Met Pro Lys Thr Gly Phe Leu Ile Ile Val
1               5                   10

<210> SEQ ID NO 9
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 9

Met Pro Lys Thr Gly Phe Leu Ile Ile Ile
1               5                   10

<210> SEQ ID NO 10
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 10

Met Pro Lys Thr Gly Leu Leu Ile Ile Val
1               5                   10

<210> SEQ ID NO 11
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 11

Phe Pro Lys Thr Gly Leu Leu Ile Ile Val
1               5                   10

<210> SEQ ID NO 12
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 12

Val Pro Lys Thr Gly Leu Leu Ile Ile Val
1               5                   10

<210> SEQ ID NO 13
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 13

Met Pro Lys Ala Gly Leu Leu Ile Ile Val
1               5                   10

<210> SEQ ID NO 14
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 14

Met Pro Lys Thr Gly Ile Leu Ile Leu Ile 1               5                   10

<210> SEQ ID NO 15
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 15

Gly Pro Arg Ala Leu Ala Glu Thr Ser
1               5

<210> SEQ ID NO 16
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 16

Gly Pro Arg Ala Leu Ile Glu Thr Ser
1               5

<210> SEQ ID NO 17
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 17

Gly Pro Arg Ala Leu Val Glu Thr Ser
1               5

<210> SEQ ID NO 18
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 18

Gly Pro Arg Ala Leu Ala Glu Thr Ser Tyr
1               5                   10

<210> SEQ ID NO 19
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 19

Gly Pro Arg Ala Leu Ile Glu Thr Ser Tyr
1               5                   10

<210> SEQ ID NO 20
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 20

Gly Pro Arg Ala Leu Val Glu Thr Ser Tyr
1               5                   10

```
<210> SEQ ID NO 21
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 21

Glu Pro Arg Lys Leu Leu Thr Gln Asp
1               5

<210> SEQ ID NO 22
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 22

His Pro Arg Lys Leu Leu Thr Gln Asp
1               5

<210> SEQ ID NO 23
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 23

Asp Pro Lys Lys Leu Leu Thr Gln His
1               5

<210> SEQ ID NO 24
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 24

Asp Pro Lys Lys Leu Leu Thr Gln Tyr
1               5

<210> SEQ ID NO 25
<211> LENGTH: 9
<212> TYPE: PRT
<213> ORGANISM: Artificial
<220> FEATURE:
<223> OTHER INFORMATION: HLA-B7 restricted native peptide

<400> SEQUENCE: 25

His Pro Lys Lys Leu Leu Met Gln Asp
1               5

<210> SEQ ID NO 26
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 26

Glu Pro Arg Lys Leu Leu Thr Gln Asp Leu
1               5                   10
```

```
<210> SEQ ID NO 27
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 27

Glu Pro Arg Lys Leu Leu Thr Gln Asp Trp
1               5                   10

<210> SEQ ID NO 28
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 28

His Pro Arg Lys Leu Leu Thr Gln Asp Leu
1               5                   10

<210> SEQ ID NO 29
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 29

His Pro Lys Lys Leu Leu Met Gln Asp Leu
1               5                   10

<210> SEQ ID NO 30
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 30

Asp Pro Lys Lys Leu Leu Thr Gln His Phe
1               5                   10

<210> SEQ ID NO 31
<211> LENGTH: 10
<212> TYPE: PRT
<213> ORGANISM: Artificial
<220> FEATURE:
<223> OTHER INFORMATION: HLA-B7 restricted native peptide

<400> SEQUENCE: 31

Asp Pro Lys Lys Leu Leu Thr Gln Tyr Phe
1               5                   10

<210> SEQ ID NO 32
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 32

Ala Pro Lys Thr Gly Phe Leu Ile Ile
1               5
```

```
<210> SEQ ID NO 33
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 33

Met Pro Lys Thr Gly Phe Leu Ile Leu
1               5

<210> SEQ ID NO 34
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 34

Ala Pro Lys Thr Gly Leu Leu Ile Ile
1               5

<210> SEQ ID NO 35
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 35

Met Pro Lys Thr Gly Leu Leu Ile Leu
1               5

<210> SEQ ID NO 36
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 36

Phe Pro Lys Thr Gly Leu Leu Ile Leu
1               5

<210> SEQ ID NO 37
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 37

Val Pro Lys Thr Gly Leu Leu Ile Leu
1               5

<210> SEQ ID NO 38
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 38

Ala Pro Lys Ala Gly Leu Leu Ile Ile
1               5

<210> SEQ ID NO 39
```

```
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 39

Met Pro Lys Ala Gly Leu Leu Ile Leu
1               5

<210> SEQ ID NO 40
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 40

Ala Pro Lys Thr Gly Ile Leu Ile Leu
1               5

<210> SEQ ID NO 41
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 41

Ala Pro Lys Thr Gly Phe Leu Ile Ile Val
1               5                   10

<210> SEQ ID NO 42
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 42

Ala Pro Lys Thr Gly Phe Leu Ile Ile Ile
1               5                   10

<210> SEQ ID NO 43
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 43

Met Pro Lys Thr Gly Phe Leu Ile Ile Leu
1               5                   10

<210> SEQ ID NO 44
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 44

Ala Pro Lys Thr Gly Leu Leu Ile Ile Val
1               5                   10

<210> SEQ ID NO 45
<211> LENGTH: 10
```

```
<212> TYPE: PRT
<213> ORGANISM: Artificial
<220> FEATURE:
<223> OTHER INFORMATION: HLA-B7 restricted optimized peptide

<400> SEQUENCE: 45

Met Pro Lys Thr Gly Leu Leu Ile Ile Leu
1               5                   10

<210> SEQ ID NO 46
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 46

Phe Pro Lys Thr Gly Leu Leu Ile Ile Leu
1               5                   10

<210> SEQ ID NO 47
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 47

Val Pro Lys Thr Gly Leu Leu Ile Ile Leu
1               5                   10

<210> SEQ ID NO 48
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 48

Ala Pro Lys Ala Gly Leu Leu Ile Ile Val
1               5                   10

<210> SEQ ID NO 49
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 49

Met Pro Lys Ala Gly Leu Leu Ile Ile Leu
1               5                   10

<210> SEQ ID NO 50
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 50

Ala Pro Lys Thr Gly Ile Leu Ile Leu Ile
1               5                   10

<210> SEQ ID NO 51
<211> LENGTH: 10
<212> TYPE: PRT
```

```
<213> ORGANISM: Artificial
<220> FEATURE:
<223> OTHER INFORMATION: HLA-B7 restricted optimized peptide

<400> SEQUENCE: 51

Met Pro Lys Thr Gly Ile Leu Ile Leu Leu
1               5                   10

<210> SEQ ID NO 52
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 52

Gly Pro Arg Ala Leu Ala Glu Thr Leu
1               5

<210> SEQ ID NO 53
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 53

Gly Pro Arg Ala Leu Ile Glu Thr Leu
1               5

<210> SEQ ID NO 54
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 54

Gly Pro Arg Ala Leu Val Glu Thr Leu
1               5

<210> SEQ ID NO 55
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 55

Gly Pro Arg Ala Leu Ala Glu Thr Ser Leu
1               5                   10

<210> SEQ ID NO 56
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 56

Gly Pro Arg Ala Leu Ile Glu Thr Ser Leu
1               5                   10

<210> SEQ ID NO 57
<211> LENGTH: 10
<212> TYPE: PRT
<213> ORGANISM: Artificial
```

```
<220> FEATURE:
<223> OTHER INFORMATION: HLA-B7 restricted optimized peptide

<400> SEQUENCE: 57

Gly Pro Arg Ala Leu Val Glu Thr Ser Leu
1               5                   10

<210> SEQ ID NO 58
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 58

Glu Pro Arg Lys Leu Leu Thr Gln Leu
1               5

<210> SEQ ID NO 59
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 59

His Pro Arg Lys Leu Leu Thr Gln Leu
1               5

<210> SEQ ID NO 60
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 60

Asp Pro Lys Lys Leu Leu Thr Gln Leu
1               5

<210> SEQ ID NO 61
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 61

Asp Pro Lys Lys Leu Leu Thr Gln Leu
1               5

<210> SEQ ID NO 62
<211> LENGTH: 9
<212> TYPE: PRT
<213> ORGANISM: Artificial
<220> FEATURE:
<223> OTHER INFORMATION: HLA-B7 restricted optimized peptide

<400> SEQUENCE: 62

His Pro Lys Lys Leu Leu Met Gln Leu
1               5

<210> SEQ ID NO 63
<211> LENGTH: 10
<212> TYPE: PRT
<213> ORGANISM: Artificial
<220> FEATURE:
```

```
<223> OTHER INFORMATION: HLA-B7 restricted optimized peptide

<400> SEQUENCE: 63

Glu Pro Arg Lys Leu Leu Thr Gln Asp Leu
1               5                   10

<210> SEQ ID NO 64
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 64

Ala Pro Arg Lys Leu Leu Thr Gln Asp Leu
1               5                   10

<210> SEQ ID NO 65
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 65

Ala Pro Lys Lys Leu Leu Met Gln Asp Leu
1               5                   10

<210> SEQ ID NO 66
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 66

Asp Pro Lys Lys Leu Leu Thr Gln His Leu
1               5                   10

<210> SEQ ID NO 67
<211> LENGTH: 10
<212> TYPE: PRT
<213> ORGANISM: Artificial
<220> FEATURE:
<223> OTHER INFORMATION: HLA-B7 restricted optimized peptide

<400> SEQUENCE: 67

Asp Pro Lys Lys Leu Leu Thr Gln Tyr Leu
1               5                   10

<210> SEQ ID NO 68
<211> LENGTH: 9
<212> TYPE: PRT
<213> ORGANISM: Artificial
<220> FEATURE:
<223> OTHER INFORMATION: HLA-A2 epitope

<400> SEQUENCE: 68

Ala Ala Gly Ile Gly Ile Leu Thr Val
1               5

<210> SEQ ID NO 69
<211> LENGTH: 10
<212> TYPE: PRT
<213> ORGANISM: Artificial
<220> FEATURE:
<223> OTHER INFORMATION: HLA-A2 epitope
```

<400> SEQUENCE: 69

Glu Ala Ala Gly Ile Gly Ile Leu Thr Val
1               5                   10

<210> SEQ ID NO 70
<211> LENGTH: 10
<212> TYPE: PRT
<213> ORGANISM: Artificial
<220> FEATURE:
<223> OTHER INFORMATION: HLA-A2 epitope

<400> SEQUENCE: 70

Ala Met Leu Gly Thr His Thr Met Glu Val
1               5                   10

<210> SEQ ID NO 71
<211> LENGTH: 9
<212> TYPE: PRT
<213> ORGANISM: Artificial
<220> FEATURE:
<223> OTHER INFORMATION: HLA-A2 epitope

<400> SEQUENCE: 71

Met Leu Gly Thr His Thr Met Glu Val
1               5

<210> SEQ ID NO 72
<211> LENGTH: 9
<212> TYPE: PRT
<213> ORGANISM: Artificial
<220> FEATURE:
<223> OTHER INFORMATION: HLA-A2 epitope

<400> SEQUENCE: 72

Lys Thr Trp Gly Gln Tyr Trp Gln Val
1               5

<210> SEQ ID NO 73
<211> LENGTH: 10
<212> TYPE: PRT
<213> ORGANISM: Artificial
<220> FEATURE:
<223> OTHER INFORMATION: HLA-A2 epitope

<400> SEQUENCE: 73

Ser Leu Ala Asp Thr Asn Ser Leu Ala Val
1               5                   10

<210> SEQ ID NO 74
<211> LENGTH: 8
<212> TYPE: PRT
<213> ORGANISM: Artificial
<220> FEATURE:
<223> OTHER INFORMATION: HLA-A2 epitope

<400> SEQUENCE: 74

Thr Asp Gln Val Pro Phe Ser Val
1               5

<210> SEQ ID NO 75
<211> LENGTH: 10
<212> TYPE: PRT
<213> ORGANISM: Artificial
<220> FEATURE:
<223> OTHER INFORMATION: HLA-A2 epitope

```
<400> SEQUENCE: 75

Val Leu Tyr Arg Tyr Gly Ser Phe Ser Val
1               5                   10

<210> SEQ ID NO 76
<211> LENGTH: 10
<212> TYPE: PRT
<213> ORGANISM: Artificial
<220> FEATURE:
<223> OTHER INFORMATION: HLA-A2 epitope

<400> SEQUENCE: 76

Leu Leu Asp Gly Thr Ala Thr Leu Arg Leu
1               5                   10

<210> SEQ ID NO 77
<211> LENGTH: 9
<212> TYPE: PRT
<213> ORGANISM: Artificial
<220> FEATURE:
<223> OTHER INFORMATION: HLA-A2 epitope

<400> SEQUENCE: 77

Gln Leu Met Pro Tyr Gly Cys Leu Leu
1               5

<210> SEQ ID NO 78
<211> LENGTH: 9
<212> TYPE: PRT
<213> ORGANISM: Artificial
<220> FEATURE:
<223> OTHER INFORMATION: HLA-A2 epitope

<400> SEQUENCE: 78

Lys Ile Phe Gly Ser Leu Ala Phe Leu
1               5

<210> SEQ ID NO 79
<211> LENGTH: 9
<212> TYPE: PRT
<213> ORGANISM: Artificial
<220> FEATURE:
<223> OTHER INFORMATION: HLA-A2 epitope

<400> SEQUENCE: 79

Cys Leu Thr Ser Thr Val Gln Leu Val
1               5

<210> SEQ ID NO 80
<211> LENGTH: 8
<212> TYPE: PRT
<213> ORGANISM: Artificial
<220> FEATURE:
<223> OTHER INFORMATION: HLA-A2 epitope

<400> SEQUENCE: 80

His Leu Tyr Gln Gly Cys Gln Trp
1               5

<210> SEQ ID NO 81
<211> LENGTH: 10
<212> TYPE: PRT
<213> ORGANISM: Artificial
<220> FEATURE:
<223> OTHER INFORMATION: HLA-A2 epitope

<400> SEQUENCE: 81
```

Val Met Ala Gly Val Gly Ser Pro Tyr Val
1               5                   10

<210> SEQ ID NO 82
<211> LENGTH: 8
<212> TYPE: PRT
<213> ORGANISM: Artificial
<220> FEATURE:
<223> OTHER INFORMATION: HLA-A2 epitope

<400> SEQUENCE: 82

Ala Leu Cys Arg Trp Gly Leu Leu
1               5

<210> SEQ ID NO 83
<211> LENGTH: 9
<212> TYPE: PRT
<213> ORGANISM: Artificial
<220> FEATURE:
<223> OTHER INFORMATION: HLA-A2 epitope

<400> SEQUENCE: 83

Val Leu Val Lys Ser Pro Asn His Val
1               5

<210> SEQ ID NO 84
<211> LENGTH: 9
<212> TYPE: PRT
<213> ORGANISM: Artificial
<220> FEATURE:
<223> OTHER INFORMATION: HLA-A2 epitope

<400> SEQUENCE: 84

Ile Leu Leu Val Val Val Leu Gly Val
1               5

<210> SEQ ID NO 85
<211> LENGTH: 9
<212> TYPE: PRT
<213> ORGANISM: Artificial
<220> FEATURE:
<223> OTHER INFORMATION: HLA-A2 epitope

<400> SEQUENCE: 85

Pro Leu Thr Ser Ile Ile Ser Ala Val
1               5

<210> SEQ ID NO 86
<211> LENGTH: 9
<212> TYPE: PRT
<213> ORGANISM: Artificial
<220> FEATURE:
<223> OTHER INFORMATION: HLA-A2 epitope

<400> SEQUENCE: 86

Ala Leu Ile His His Asn Thr His Leu
1               5

<210> SEQ ID NO 87
<211> LENGTH: 9
<212> TYPE: PRT
<213> ORGANISM: Artificial
<220> FEATURE:
<223> OTHER INFORMATION: HLA-A2 epitope

<400> SEQUENCE: 87

Thr Leu Glu Glu Ile Thr Gly Tyr Leu
1               5

<210> SEQ ID NO 88
<211> LENGTH: 9
<212> TYPE: PRT
<213> ORGANISM: Artificial
<220> FEATURE:
<223> OTHER INFORMATION: HLA-A2 epitope

<400> SEQUENCE: 88

Pro Leu Gln Pro Glu Gln Leu Gln Val
1               5

<210> SEQ ID NO 89
<211> LENGTH: 9
<212> TYPE: PRT
<213> ORGANISM: Artificial
<220> FEATURE:
<223> OTHER INFORMATION: HLA-A2 epitope

<400> SEQUENCE: 89

Glu Leu Val Ser Glu Phe Ser Arg Met
1               5

<210> SEQ ID NO 90
<211> LENGTH: 9
<212> TYPE: PRT
<213> ORGANISM: Artificial
<220> FEATURE:
<223> OTHER INFORMATION: HLA-A2 epitope

<400> SEQUENCE: 90

Asp Met Pro Ile Tyr Met Tyr Ser Val
1               5

<210> SEQ ID NO 91
<211> LENGTH: 10
<212> TYPE: PRT
<213> ORGANISM: Artificial
<220> FEATURE:
<223> OTHER INFORMATION: HLA-A2 epitope

<400> SEQUENCE: 91

Thr Val Trp Glu Leu Met Thr Phe Gly Ala
1               5                   10

<210> SEQ ID NO 92
<211> LENGTH: 10
<212> TYPE: PRT
<213> ORGANISM: Artificial
<220> FEATURE:
<223> OTHER INFORMATION: HLA-A2 epitope

<400> SEQUENCE: 92

Thr Ile Trp Glu Leu Met Thr Phe Gly Gly
1               5                   10

<210> SEQ ID NO 93
<211> LENGTH: 10
<212> TYPE: PRT
<213> ORGANISM: Artificial
<220> FEATURE:
<223> OTHER INFORMATION: HLA-A2 epitope

<400> SEQUENCE: 93

Thr Val Trp Glu Leu Met Thr Phe Gly Ser

```
<210> SEQ ID NO 94
<211> LENGTH: 9
<212> TYPE: PRT
<213> ORGANISM: Artificial
<220> FEATURE:
<223> OTHER INFORMATION: HLA-A2 epitope

<400> SEQUENCE: 94

Lys Val Lys Val Leu Gly Ser Gly Ala
1               5

<210> SEQ ID NO 95
<211> LENGTH: 9
<212> TYPE: PRT
<213> ORGANISM: Artificial
<220> FEATURE:
<223> OTHER INFORMATION: HLA-A2 epitope

<400> SEQUENCE: 95

Lys Leu Lys Val Leu Gly Ser Gly Val
1               5

<210> SEQ ID NO 96
<211> LENGTH: 9
<212> TYPE: PRT
<213> ORGANISM: Artificial
<220> FEATURE:
<223> OTHER INFORMATION: HLA-A2 epitope

<400> SEQUENCE: 96

Arg Val Lys Val Leu Gly Ser Gly Ala
1               5

<210> SEQ ID NO 97
<211> LENGTH: 9
<212> TYPE: PRT
<213> ORGANISM: Artificial
<220> FEATURE:
<223> OTHER INFORMATION: HLA-A2 epitope

<400> SEQUENCE: 97

Lys Ile Lys Val Leu Gly Ser Gly Ala
1               5

<210> SEQ ID NO 98
<211> LENGTH: 9
<212> TYPE: PRT
<213> ORGANISM: Artificial
<220> FEATURE:
<223> OTHER INFORMATION: HLA-A2 epitope

<400> SEQUENCE: 98

Asp Leu Ala Ala Arg Asn Val Leu Val
1               5

<210> SEQ ID NO 99
<211> LENGTH: 9
<212> TYPE: PRT
<213> ORGANISM: Artificial
<220> FEATURE:
<223> OTHER INFORMATION: HLA-A2 epitope

<400> SEQUENCE: 99

Asn Leu Ala Ala Arg Asn Val Leu Leu
1               5
```

```
<210> SEQ ID NO 100
<211> LENGTH: 9
<212> TYPE: PRT
<213> ORGANISM: Artificial
<220> FEATURE:
<223> OTHER INFORMATION: HLA-A2 epitope

<400> SEQUENCE: 100

Asp Val Trp Ser Tyr Gly Val Thr Val
1               5

<210> SEQ ID NO 101
<211> LENGTH: 9
<212> TYPE: PRT
<213> ORGANISM: Artificial
<220> FEATURE:
<223> OTHER INFORMATION: HLA-A2 epitope

<400> SEQUENCE: 101

Asp Val Trp Ser Tyr Gly Val Thr Ile
1               5

<210> SEQ ID NO 102
<211> LENGTH: 9
<212> TYPE: PRT
<213> ORGANISM: Artificial
<220> FEATURE:
<223> OTHER INFORMATION: HLA-A2 epitope

<400> SEQUENCE: 102

Asp Leu Leu Glu Lys Gly Glu Arg Leu
1               5

<210> SEQ ID NO 103
<211> LENGTH: 10
<212> TYPE: PRT
<213> ORGANISM: Artificial
<220> FEATURE:
<223> OTHER INFORMATION: HLA-A2 epitope

<400> SEQUENCE: 103

Ser Ile Leu Glu Leu Lys Gly Glu Arg Leu
1               5                   10

<210> SEQ ID NO 104
<211> LENGTH: 10
<212> TYPE: PRT
<213> ORGANISM: Artificial
<220> FEATURE:
<223> OTHER INFORMATION: HLA-A2 epitope

<400> SEQUENCE: 104

Pro Ile Cys Thr Ile Asp Val Tyr Met Ile
1               5                   10

<210> SEQ ID NO 105
<211> LENGTH: 10
<212> TYPE: PRT
<213> ORGANISM: Artificial
<220> FEATURE:
<223> OTHER INFORMATION: HLA-A2 epitope

<400> SEQUENCE: 105

Gln Ile Cys Thr Ile Asp Val Tyr Met Val
1               5                   10
```

```
<210> SEQ ID NO 106
<211> LENGTH: 10
<212> TYPE: PRT
<213> ORGANISM: Artificial
<220> FEATURE:
<223> OTHER INFORMATION: HLA-A2 epitope

<400> SEQUENCE: 106

Pro Ile Cys Thr Ile Asp Val Tyr Met Val
1               5                   10

<210> SEQ ID NO 107
<211> LENGTH: 10
<212> TYPE: PRT
<213> ORGANISM: Artificial
<220> FEATURE:
<223> OTHER INFORMATION: HLA-A2 epitope

<400> SEQUENCE: 107

Pro Ile Cys Thr Ile Asp Val Tyr Lys Ile
1               5                   10

<210> SEQ ID NO 108
<211> LENGTH: 9
<212> TYPE: PRT
<213> ORGANISM: Artificial
<220> FEATURE:
<223> OTHER INFORMATION: HLA-A2 epitope

<400> SEQUENCE: 108

Tyr Leu Glu Tyr Arg Gln Val Pro Gly
1               5

<210> SEQ ID NO 109
<211> LENGTH: 9
<212> TYPE: PRT
<213> ORGANISM: Artificial
<220> FEATURE:
<223> OTHER INFORMATION: HLA-A2 epitope

<400> SEQUENCE: 109

Tyr Leu Glu Tyr Arg Gln Val Pro Asp
1               5

<210> SEQ ID NO 110
<211> LENGTH: 10
<212> TYPE: PRT
<213> ORGANISM: Artificial
<220> FEATURE:
<223> OTHER INFORMATION: HLA-A2 epitope

<400> SEQUENCE: 110

Asp Leu Gln Val Asn Ser Leu Gln Thr Val
1               5                   10

<210> SEQ ID NO 111
<211> LENGTH: 9
<212> TYPE: PRT
<213> ORGANISM: Artificial
<220> FEATURE:
<223> OTHER INFORMATION: HLA-A2 epitope

<400> SEQUENCE: 111

Arg Leu Phe Phe Tyr Arg Lys Ser Val
1               5
```

```
<210> SEQ ID NO 112
<211> LENGTH: 9
<212> TYPE: PRT
<213> ORGANISM: Artificial
<220> FEATURE:
<223> OTHER INFORMATION: HLA-A2 epitope

<400> SEQUENCE: 112

Tyr Ala Gly Ile Gly Ile Leu Thr Val
1               5

<210> SEQ ID NO 113
<211> LENGTH: 10
<212> TYPE: PRT
<213> ORGANISM: Artificial
<220> FEATURE:
<223> OTHER INFORMATION: HLA-A2 epitope

<400> SEQUENCE: 113

Glu Leu Ala Gly Ile Gly Ile Leu Thr Val
1               5                   10

<210> SEQ ID NO 114
<211> LENGTH: 10
<212> TYPE: PRT
<213> ORGANISM: Artificial
<220> FEATURE:
<223> OTHER INFORMATION: HLA-A2 epitope

<400> SEQUENCE: 114

Tyr Met Leu Gly Thr His Thr Met Glu Val
1               5                   10

<210> SEQ ID NO 115
<211> LENGTH: 9
<212> TYPE: PRT
<213> ORGANISM: Artificial
<220> FEATURE:
<223> OTHER INFORMATION: HLA-A2 epitope

<400> SEQUENCE: 115

Tyr Leu Gly Thr His Thr Met Glu Val
1               5

<210> SEQ ID NO 116
<211> LENGTH: 9
<212> TYPE: PRT
<213> ORGANISM: Artificial
<220> FEATURE:
<223> OTHER INFORMATION: HLA-A2 epitope

<400> SEQUENCE: 116

Tyr Thr Trp Gly Gln Tyr Trp Gln Val
1               5

<210> SEQ ID NO 117
<211> LENGTH: 9
<212> TYPE: PRT
<213> ORGANISM: Artificial
<220> FEATURE:
<223> OTHER INFORMATION: HLA-A2 epitope

<400> SEQUENCE: 117

Lys Met Trp Gly Gln Tyr Trp Gln Val
1               5

<210> SEQ ID NO 118
```

```
<211> LENGTH: 10
<212> TYPE: PRT
<213> ORGANISM: Artificial
<220> FEATURE:
<223> OTHER INFORMATION: HLA-A2 epitope

<400> SEQUENCE: 118

Tyr Leu Ala Asp Thr Asn Ser Leu Ala Val
1               5                   10

<210> SEQ ID NO 119
<211> LENGTH: 8
<212> TYPE: PRT
<213> ORGANISM: Artificial
<220> FEATURE:
<223> OTHER INFORMATION: HLA-A2 epitope

<400> SEQUENCE: 119

Tyr Asp Gln Val Pro Phe Ser Val
1               5

<210> SEQ ID NO 120
<211> LENGTH: 8
<212> TYPE: PRT
<213> ORGANISM: Artificial
<220> FEATURE:
<223> OTHER INFORMATION: HLA-A2 epitope

<400> SEQUENCE: 120

Tyr Met Gln Val Pro Phe Ser Val
1               5

<210> SEQ ID NO 121
<211> LENGTH: 10
<212> TYPE: PRT
<213> ORGANISM: Artificial
<220> FEATURE:
<223> OTHER INFORMATION: HLA-A2 epitope

<400> SEQUENCE: 121

Tyr Leu Tyr Arg Tyr Gly Ser Phe Ser Val
1               5                   10

<210> SEQ ID NO 122
<211> LENGTH: 10
<212> TYPE: PRT
<213> ORGANISM: Artificial
<220> FEATURE:
<223> OTHER INFORMATION: HLA-A2 epitope

<400> SEQUENCE: 122

Tyr Leu Asp Gly Thr Ala Thr Leu Arg Leu
1               5                   10

<210> SEQ ID NO 123
<211> LENGTH: 9
<212> TYPE: PRT
<213> ORGANISM: Artificial
<220> FEATURE:
<223> OTHER INFORMATION: HLA-A2 epitope

<400> SEQUENCE: 123

Tyr Leu Met Pro Tyr Gly Cys Leu Leu
1               5

<210> SEQ ID NO 124
<211> LENGTH: 9
```

```
<212> TYPE: PRT
<213> ORGANISM: Artificial
<220> FEATURE:
<223> OTHER INFORMATION: HLA-A2 epitope

<400> SEQUENCE: 124

Tyr Ile Phe Gly Ser Leu Ala Phe Leu
1               5

<210> SEQ ID NO 125
<211> LENGTH: 9
<212> TYPE: PRT
<213> ORGANISM: Artificial
<220> FEATURE:
<223> OTHER INFORMATION: HLA-A2 epitope

<400> SEQUENCE: 125

Tyr Leu Thr Ser Thr Val Gln Leu Val
1               5

<210> SEQ ID NO 126
<211> LENGTH: 8
<212> TYPE: PRT
<213> ORGANISM: Artificial
<220> FEATURE:
<223> OTHER INFORMATION: HLA-A2 epitope

<400> SEQUENCE: 126

Tyr Leu Tyr Gln Gly Cys Gln Trp
1               5

<210> SEQ ID NO 127
<211> LENGTH: 10
<212> TYPE: PRT
<213> ORGANISM: Artificial
<220> FEATURE:
<223> OTHER INFORMATION: HLA-A2 epitope

<400> SEQUENCE: 127

Tyr Met Ala Gly Val Gly Ser Pro Tyr Val
1               5                   10

<210> SEQ ID NO 128
<211> LENGTH: 8
<212> TYPE: PRT
<213> ORGANISM: Artificial
<220> FEATURE:
<223> OTHER INFORMATION: HLA-A2 epitope

<400> SEQUENCE: 128

Tyr Leu Cys Arg Trp Gly Leu Leu
1               5

<210> SEQ ID NO 129
<211> LENGTH: 9
<212> TYPE: PRT
<213> ORGANISM: Artificial
<220> FEATURE:
<223> OTHER INFORMATION: HLA-A2 epitope

<400> SEQUENCE: 129

Tyr Leu Val Lys Ser Pro Asn His Val
1               5

<210> SEQ ID NO 130
<211> LENGTH: 9
<212> TYPE: PRT
```

```
<213> ORGANISM: Artificial
<220> FEATURE:
<223> OTHER INFORMATION: HLA-A2 epitope

<400> SEQUENCE: 130

Tyr Leu Leu Val Val Val Leu Gly Val
1               5

<210> SEQ ID NO 131
<211> LENGTH: 9
<212> TYPE: PRT
<213> ORGANISM: Artificial
<220> FEATURE:
<223> OTHER INFORMATION: HLA-A2 epitope

<400> SEQUENCE: 131

Tyr Leu Thr Ser Ile Ile Ser Ala Val
1               5

<210> SEQ ID NO 132
<211> LENGTH: 9
<212> TYPE: PRT
<213> ORGANISM: Artificial
<220> FEATURE:
<223> OTHER INFORMATION: HLA-A2 epitope

<400> SEQUENCE: 132

Tyr Leu Ile His His Asn Thr His Leu
1               5

<210> SEQ ID NO 133
<211> LENGTH: 9
<212> TYPE: PRT
<213> ORGANISM: Artificial
<220> FEATURE:
<223> OTHER INFORMATION: HLA-A2 epitope

<400> SEQUENCE: 133

Tyr Leu Glu Glu Ile Thr Gly Tyr Leu
1               5

<210> SEQ ID NO 134
<211> LENGTH: 9
<212> TYPE: PRT
<213> ORGANISM: Artificial
<220> FEATURE:
<223> OTHER INFORMATION: HLA-A2 epitope

<400> SEQUENCE: 134

Tyr Leu Gln Pro Glu Gln Leu Gln Val
1               5

<210> SEQ ID NO 135
<211> LENGTH: 9
<212> TYPE: PRT
<213> ORGANISM: Artificial
<220> FEATURE:
<223> OTHER INFORMATION: HLA-A2 epitope

<400> SEQUENCE: 135

Tyr Leu Val Ser Glu Phe Ser Arg Met
1               5

<210> SEQ ID NO 136
<211> LENGTH: 9
<212> TYPE: PRT
<213> ORGANISM: Artificial
```

```
<220> FEATURE:
<223> OTHER INFORMATION: HLA-A2 epitope

<400> SEQUENCE: 136

Tyr Met Pro Ile Tyr Met Tyr Ser Val
1               5

<210> SEQ ID NO 137
<211> LENGTH: 10
<212> TYPE: PRT
<213> ORGANISM: Artificial
<220> FEATURE:
<223> OTHER INFORMATION: HLA-A2 epitope

<400> SEQUENCE: 137

Tyr Val Trp Glu Leu Met Thr Phe Gly Val
1               5                   10

<210> SEQ ID NO 138
<211> LENGTH: 9
<212> TYPE: PRT
<213> ORGANISM: Artificial
<220> FEATURE:
<223> OTHER INFORMATION: HLA-A2 epitope

<400> SEQUENCE: 138

Tyr Val Lys Val Leu Gly Ser Gly Val
1               5

<210> SEQ ID NO 139
<211> LENGTH: 9
<212> TYPE: PRT
<213> ORGANISM: Artificial
<220> FEATURE:
<223> OTHER INFORMATION: HLA-A2 epitope

<400> SEQUENCE: 139

Tyr Leu Ala Ala Arg Asn Val Leu Val
1               5

<210> SEQ ID NO 140
<211> LENGTH: 9
<212> TYPE: PRT
<213> ORGANISM: Artificial
<220> FEATURE:
<223> OTHER INFORMATION: HLA-A2 epitope

<400> SEQUENCE: 140

Tyr Val Trp Ser Tyr Gly Val Thr Val
1               5

<210> SEQ ID NO 141
<211> LENGTH: 9
<212> TYPE: PRT
<213> ORGANISM: Artificial
<220> FEATURE:
<223> OTHER INFORMATION: HLA-A2 epitope

<400> SEQUENCE: 141

Tyr Leu Leu Glu Lys Gly Glu Arg Leu
1               5

<210> SEQ ID NO 142
<211> LENGTH: 10
<212> TYPE: PRT
<213> ORGANISM: Artificial
<220> FEATURE:
```

-continued

```
<223> OTHER INFORMATION: HLA-A2 epitope

<400> SEQUENCE: 142

Tyr Ile Cys Thr Ile Asp Val Tyr Met Val
1               5                   10

<210> SEQ ID NO 143
<211> LENGTH: 9
<212> TYPE: PRT
<213> ORGANISM: Artificial
<220> FEATURE:
<223> OTHER INFORMATION: HLA-A2 epitope

<400> SEQUENCE: 143

Tyr Leu Glu Tyr Arg Gln Val Pro Val
1               5

<210> SEQ ID NO 144
<211> LENGTH: 10
<212> TYPE: PRT
<213> ORGANISM: Artificial
<220> FEATURE:
<223> OTHER INFORMATION: HLA-A2 epitope

<400> SEQUENCE: 144

Tyr Leu Gln Val Asn Ser Leu Gln Thr Val
1               5                   10

<210> SEQ ID NO 145
<211> LENGTH: 9
<212> TYPE: PRT
<213> ORGANISM: Artificial
<220> FEATURE:
<223> OTHER INFORMATION: HLA-A2 epitope

<400> SEQUENCE: 145

Tyr Leu Phe Phe Tyr Arg Lys Ser Val
1               5

<210> SEQ ID NO 146
<211> LENGTH: 9
<212> TYPE: PRT
<213> ORGANISM: Artificial
<220> FEATURE:
<223> OTHER INFORMATION: HLA-B7 epitope

<400> SEQUENCE: 146

Asp Pro Arg Arg Leu Val Gln Leu Leu
1               5

<210> SEQ ID NO 147
<211> LENGTH: 9
<212> TYPE: PRT
<213> ORGANISM: Artificial
<220> FEATURE:
<223> OTHER INFORMATION: HLA-B7 epitope

<400> SEQUENCE: 147

Ser Pro Arg Leu Gln Leu Ser Asn Gly
1               5

<210> SEQ ID NO 148
<211> LENGTH: 9
<212> TYPE: PRT
<213> ORGANISM: Artificial
<220> FEATURE:
<223> OTHER INFORMATION: HLA-B7 epitope
```

<400> SEQUENCE: 148

Ala Pro Arg Ser Pro Leu Ala Pro Ser
1               5

<210> SEQ ID NO 149
<211> LENGTH: 9
<212> TYPE: PRT
<213> ORGANISM: Artificial
<220> FEATURE:
<223> OTHER INFORMATION: HLA-B7 epitope

<400> SEQUENCE: 149

Ser Pro Lys Ala Asn Lys Glu Ile Leu
1               5

<210> SEQ ID NO 150
<211> LENGTH: 9
<212> TYPE: PRT
<213> ORGANISM: Artificial
<220> FEATURE:
<223> OTHER INFORMATION: HLA-B7 epitope

<400> SEQUENCE: 150

Gly Pro Lys His Ser Asp Cys Leu Ala
1               5

<210> SEQ ID NO 151
<211> LENGTH: 9
<212> TYPE: PRT
<213> ORGANISM: Artificial
<220> FEATURE:
<223> OTHER INFORMATION: HLA-B7 epitope

<400> SEQUENCE: 151

Ala Pro Arg Arg Leu Val Gln Leu Leu
1               5

<210> SEQ ID NO 152
<211> LENGTH: 9
<212> TYPE: PRT
<213> ORGANISM: Artificial
<220> FEATURE:
<223> OTHER INFORMATION: HLA-B7 epitope

<400> SEQUENCE: 152

Ser Pro Arg Leu Gln Leu Ser Asn Leu
1               5

<210> SEQ ID NO 153
<211> LENGTH: 9
<212> TYPE: PRT
<213> ORGANISM: Artificial
<220> FEATURE:
<223> OTHER INFORMATION: HLA-B7 epitope

<400> SEQUENCE: 153

Ala Pro Arg Ser Pro Leu Ala Pro Leu
1               5

<210> SEQ ID NO 154
<211> LENGTH: 9
<212> TYPE: PRT
<213> ORGANISM: Artificial
<220> FEATURE:
<223> OTHER INFORMATION: HLA-B7 epitope

```
<400> SEQUENCE: 154

Ala Pro Lys Ala Asn Lys Glu Ile Leu
1               5

<210> SEQ ID NO 155
<211> LENGTH: 9
<212> TYPE: PRT
<213> ORGANISM: Artificial
<220> FEATURE:
<223> OTHER INFORMATION: HLA-B7 epitope

<400> SEQUENCE: 155

Ala Pro Lys His Ser Asp Cys Leu Ala
1               5

<210> SEQ ID NO 156
<211> LENGTH: 9
<212> TYPE: PRT
<213> ORGANISM: Artificial
<220> FEATURE:
<223> OTHER INFORMATION: HLA-A24 epitope

<400> SEQUENCE: 156

Pro Tyr Gly Val Leu Leu Lys Thr His
1               5

<210> SEQ ID NO 157
<211> LENGTH: 9
<212> TYPE: PRT
<213> ORGANISM: Artificial
<220> FEATURE:
<223> OTHER INFORMATION: HLA-A24 epitope

<400> SEQUENCE: 157

Pro Tyr Met Arg Gln Phe Val Ala His
1               5

<210> SEQ ID NO 158
<211> LENGTH: 9
<212> TYPE: PRT
<213> ORGANISM: Artificial
<220> FEATURE:
<223> OTHER INFORMATION: HLA-A24 epitope

<400> SEQUENCE: 158

Pro Tyr Val Ser Arg Leu Leu Gly Ile
1               5

<210> SEQ ID NO 159
<211> LENGTH: 9
<212> TYPE: PRT
<213> ORGANISM: Artificial
<220> FEATURE:
<223> OTHER INFORMATION: HLA-A24 epitope

<400> SEQUENCE: 159

Pro Tyr Gly Lys Gly Trp Asp Leu Met
1               5

<210> SEQ ID NO 160
<211> LENGTH: 9
<212> TYPE: PRT
<213> ORGANISM: Artificial
<220> FEATURE:
<223> OTHER INFORMATION: HLA-A24 epitope

<400> SEQUENCE: 160
```

Thr Tyr Leu Val Gln Val Gln Ala Leu
1               5

<210> SEQ ID NO 161
<211> LENGTH: 9
<212> TYPE: PRT
<213> ORGANISM: Artificial
<220> FEATURE:
<223> OTHER INFORMATION: HLA-A24 epitope

<400> SEQUENCE: 161

Pro Tyr Trp Glu Leu Ser Asn His Glu
1               5

<210> SEQ ID NO 162
<211> LENGTH: 9
<212> TYPE: PRT
<213> ORGANISM: Artificial
<220> FEATURE:
<223> OTHER INFORMATION: HLA-A24 epitope

<400> SEQUENCE: 162

Pro Tyr Asp Gly Ile Pro Ala Arg Glu
1               5

<210> SEQ ID NO 163
<211> LENGTH: 9
<212> TYPE: PRT
<213> ORGANISM: Artificial
<220> FEATURE:
<223> OTHER INFORMATION: HLA-A24 epitope

<400> SEQUENCE: 163

Arg Tyr Glu Phe Leu Trp Gly Pro Arg
1               5

<210> SEQ ID NO 164
<211> LENGTH: 9
<212> TYPE: PRT
<213> ORGANISM: Artificial
<220> FEATURE:
<223> OTHER INFORMATION: HLA-A24 epitope

<400> SEQUENCE: 164

Pro Tyr Asn Tyr Leu Ser Thr Asp Val
1               5

<210> SEQ ID NO 165
<211> LENGTH: 9
<212> TYPE: PRT
<213> ORGANISM: Artificial
<220> FEATURE:
<223> OTHER INFORMATION: HLA-A24 epitope

<400> SEQUENCE: 165

Lys Tyr Gly Val Leu Leu Lys Thr Leu
1               5

<210> SEQ ID NO 166
<211> LENGTH: 9
<212> TYPE: PRT
<213> ORGANISM: Artificial
<220> FEATURE:
<223> OTHER INFORMATION: HLA-A24 epitope

<400> SEQUENCE: 166

Arg Tyr Met Arg Gln Phe Val Ala Leu
1               5

<210> SEQ ID NO 167
<211> LENGTH: 9
<212> TYPE: PRT
<213> ORGANISM: Artificial
<220> FEATURE:
<223> OTHER INFORMATION: HLA-A24 epitope

<400> SEQUENCE: 167

Arg Tyr Val Ser Arg Leu Leu Gly Ile
1               5

<210> SEQ ID NO 168
<211> LENGTH: 9
<212> TYPE: PRT
<213> ORGANISM: Artificial
<220> FEATURE:
<223> OTHER INFORMATION: HLA-A24 epitope

<400> SEQUENCE: 168

Arg Tyr Gly Lys Gly Trp Asp Leu Leu
1               5

<210> SEQ ID NO 169
<211> LENGTH: 9
<212> TYPE: PRT
<213> ORGANISM: Artificial
<220> FEATURE:
<223> OTHER INFORMATION: HLA-A24 epitope

<400> SEQUENCE: 169

Arg Tyr Leu Val Gln Val Gln Ala Leu
1               5

<210> SEQ ID NO 170
<211> LENGTH: 9
<212> TYPE: PRT
<213> ORGANISM: Artificial
<220> FEATURE:
<223> OTHER INFORMATION: HLA-A24 epitope

<400> SEQUENCE: 170

Arg Tyr Trp Glu Leu Ser Asn His Leu
1               5

<210> SEQ ID NO 171
<211> LENGTH: 9
<212> TYPE: PRT
<213> ORGANISM: Artificial
<220> FEATURE:
<223> OTHER INFORMATION: MAGE-A A1L9 peptide

<400> SEQUENCE: 171

Ala Pro Arg Ala Leu Val Glu Thr Leu
1               5

<210> SEQ ID NO 172
<211> LENGTH: 10
<212> TYPE: PRT
<213> ORGANISM: Artificial
<220> FEATURE:
<223> OTHER INFORMATION: Reference peptide CMV265-274

<400> SEQUENCE: 172

Arg Pro His Glu Arg Asn Gly Phe Thr Val

```
<210> SEQ ID NO 173
<211> LENGTH: 13
<212> TYPE: PRT
<213> ORGANISM: Artificial
<220> FEATURE:
<223> OTHER INFORMATION: I-Ab restricted HBVcore128 T helper epitope

<400> SEQUENCE: 173

Thr Pro Pro Ala Tyr Arg Pro Pro Asn Ala Pro Ile Leu
1               5                   10

<210> SEQ ID NO 174
<211> LENGTH: 103
<212> TYPE: PRT
<213> ORGANISM: Homo sapiens

<400> SEQUENCE: 174

Ser Leu Ala Gln Gln Cys Val Ala Thr Pro Leu Gly Glu Thr Gly Thr
1               5                   10                  15

Asp Gln Ala Pro Phe Arg Gln Pro Ser Ser Arg Ser Thr Ser Cys Ile
                20                  25                  30

Leu Arg Val Thr Lys Val Ala Asp Gly Ile Lys Tyr Lys His Cys Glu
            35                  40                  45

Gly Ser Asp Lys Ala Asp Thr Gly Ser Val Ile Phe Val Met Met Gly
50                  55                  60

His Glu Val Met Tyr Asp His Ala Tyr Gly Leu Thr Lys Asp Arg Ala
65                  70                  75                  80

Asx Tyr Val Ile Val Ser Ala Arg Val Arg Phe Phe Phe Ser Leu Arg
                85                  90                  95

Glu Ala Arg Glu Glu Gly Val
            100

<210> SEQ ID NO 175
<211> LENGTH: 314
<212> TYPE: PRT
<213> ORGANISM: Homo sapiens

<400> SEQUENCE: 175

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Glu Gln Gln Thr Ala Ser Ser Ser Thr Leu Val Glu Val
            35                  40                  45

Thr Leu Gly Glu Val Pro Ala Ala Asp Ser Pro Ser Pro His Ser
    50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
            115                 120                 125

Pro Val Thr Lys Ala Glu Met Leu Glu Ser Val Leu Arg Asn Cys Gln
        130                 135                 140
```

```
Asp Phe Phe Pro Val Ile Phe Ser Lys Ala Ser Glu Tyr Leu Gln Leu
145                 150                 155                 160

Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Glu Lys Ile Trp Glu Glu
    210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Ile Glu Thr Ser Tyr Val Lys Val Leu His
            275                 280                 285

His Thr Leu Lys Ile Gly Gly Glu Pro His Ile Ser Tyr Pro Pro Leu
        290                 295                 300

His Glu Arg Ala Leu Arg Glu Gly Glu Glu
305                 310

<210> SEQ ID NO 176
<211> LENGTH: 49
<212> TYPE: PRT
<213> ORGANISM: Homo sapiens

<400> SEQUENCE: 176

Glu Ala Glu Asp Gln Leu Pro Met Pro Ser Tyr Asp Ser Thr Leu Val
1               5                   10                  15

Ala Gly Val Gly Trp Tyr Ser Ser Leu Met Asp Gly Phe Ala Ile Ala
            20                  25                  30

Arg Val Ile Leu Gly Asp Lys Thr His Phe Val Met Val Ser Gly Trp
        35                  40                  45

Val

<210> SEQ ID NO 177
<211> LENGTH: 105
<212> TYPE: PRT
<213> ORGANISM: Homo sapiens

<400> SEQUENCE: 177

Ser Ser Lys Val Gln Glu Thr Glu Ala Val Pro Pro Gly Glu Ala
1               5                   10                  15

Gly Gln Ala Leu Pro Ser Phe Cys Pro Asn Ser Ser Thr Ser Ala Leu
            20                  25                  30

Arg Glu Leu Asn Val Asp Ala Arg Lys Leu Arg Ile Lys Tyr Lys Arg
        35                  40                  45

Cys Gly Ser Lys Met Ile Asp Lys Asp Ala Asn Thr Thr Asn Ile Phe
    50                  55                  60

Gly Thr Met Ser Ser Glu Gly Val Met Tyr Asp His Thr Tyr Gly Glu
65                  70                  75                  80

Thr Trp Asn Arg Ala Glu Val Val Arg Val Asn Ala Arg Val Arg Ala
                85                  90                  95

Ser Arg Glu Ala Leu Glu Glu Gly Val
```

<210> SEQ ID NO 178
<211> LENGTH: 51
<212> TYPE: PRT
<213> ORGANISM: Homo sapiens

<400> SEQUENCE: 178

Glu Ala Glu Asp Gln Leu Pro Met Pro Ser Tyr Asp Ser Thr Leu Val
1               5                   10                  15

Ala Lys Gly Val Gly Trp Tyr Asp Ser Leu Met Asp Gly Val Phe Ala
            20                  25                  30

Ile Phe Ile Lys Val Ile Gly Asp Lys Thr Tyr Phe Met Val Ser Gly
        35                  40                  45

Arg Leu Trp
    50

<210> SEQ ID NO 179
<211> LENGTH: 37
<212> TYPE: PRT
<213> ORGANISM: Homo sapiens

<400> SEQUENCE: 179

Gln Glu Arg Glu Thr Leu Pro Ser Glu Gln Ser Thr Thr Ser Val Leu
1               5                   10                  15

Ala Phe Gly Ile Phe Arg Gly Ile Val Lys Val Ala Ser Asp Thr Val
            20                  25                  30

Leu Ser Gly Trp Phe
        35

<210> SEQ ID NO 180
<211> LENGTH: 200
<212> TYPE: PRT
<213> ORGANISM: Homo sapiens

<400> SEQUENCE: 180

Arg Ala Pro Lys Arg Met Asp Gln Ser Gln Ser Thr Gln Glu Leu
1               5                   10                  15

Ala Val Glu Asp Ala Ser Thr Ser Ser Ser Phe Pro Ser Ser Phe Pro
            20                  25                  30

Ser Ser Ser Ser Ser Ser Ser Cys Tyr Pro Ile Pro Ser Pro
        35                  40                  45

Glu Ser Asp Glu Thr Asn Gln Ala Ile Cys Ser Pro Ser Val Val Ala
    50                  55                  60

Ser Leu Pro Leu Asp Ser Lys Ser Ser Thr Leu Gln Val Leu Ser Leu
65                  70                  75                  80

Pro Arg Ser Glu Asp Glu Val Thr Asp Gln Phe Gln Met Lys Ile Ile
                85                  90                  95

Ile Lys Tyr Glu His Leu Leu Glu Cys Met Leu Asp Lys Asp Thr Gly
            100                 105                 110

Ser Phe Val Ser Thr Met Ser Val Ser Ile Leu Ile Ser Phe Tyr Thr
        115                 120                 125

Val Ala Asn Met Gly Leu Tyr Asp Met His Leu Ile Tyr Gly Glu Thr
    130                 135                 140

Trp Arg His Ala Ile Arg Lys Met Ser Leu Lys Phe Leu Ala Val Asn
145                 150                 155                 160

Ser Asp Pro Arg Phe Leu Trp Tyr Glu Lys Asp Glu Arg Ala Gln Asp
                165                 170                 175

```
Arg Ile Ala Thr Thr Asp Asp Thr Thr Ala Met Ala Ser Ala Ser Ser
            180                 185                 190

Ser Ala Thr Gly Ser Tyr Pro Glu
        195                 200
```